(12) United States Patent
Mukherjee et al.

(10) Patent No.: US 8,084,415 B2
(45) Date of Patent: Dec. 27, 2011

(54) UTEROGLOBIN IN THE TREATMENT OF IGA MEDIATED NEPHROPATHY

(75) Inventors: Anil B. Mukherjee, Brookeville, MD (US); Feng Zheng, Rockville, MD (US); Zhongjian Zhang, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 853 days.

(21) Appl. No.: 11/934,050

(22) Filed: Nov. 1, 2007

(65) Prior Publication Data

US 2009/0029908 A1 Jan. 29, 2009

Related U.S. Application Data

(63) Continuation of application No. 10/019,833, filed as application No. PCT/US00/09979 on Apr. 13, 2000, now abandoned.

(60) Provisional application No. 60/130,434, filed on Apr. 21, 1999.

(51) Int. Cl.
*A61K 38/17* (2006.01)
*C07K 14/435* (2006.01)

(52) U.S. Cl. .............................. 514/2; 514/12
(58) Field of Classification Search .................. None
See application file for complete search history.

(56) References Cited

U.S. PATENT DOCUMENTS

| 5,696,092 | A | 12/1997 | Patierno et al. | |
| 6,255,281 | B1 * | 7/2001 | Pilon et al. | 514/12 |
| 2002/0006640 | A1 * | 1/2002 | Ni et al. | 435/69.1 |

FOREIGN PATENT DOCUMENTS

| WO | WO 98/53846 | 12/1998 |
| WO | WO 01/32677 | 5/2001 |

OTHER PUBLICATIONS

Attwood, Science, 2000, vol. 290, p. 471-473.
Cederholm et al., PNAS, 1988, vol. 85, p. 4865-4868.
DeMayo, "Advantages and Pitfalls of Transgenic and Mutant Animals," *American Journal of Kidney Diseases*, vol. 33, No. 3, pp. 598-600 (1999).
Hildebrandt et al., "Familial Fibrillary Glomerulopathies: What is the Role of Fibronectin?" *Advances in Nephrology*, vol. 28, pp. 429-437 (1998).

Kundu, Gopal C., et al., "Recombinant Human Uteroglobin Suppresses Cellular Invasiveness via a Novel Class of High-affinity Cell Surface Binding Site," *Proc. Natl. Acad. Sci. USA*, Apr. 1996, pp. 2915-2919, vol. 93.
Kundu, Gopal C., et al., "Uteroglobin (UG) Suppresses Extracellular Matrix Invasion by Normal and Cancer Cells that Express the High Affinity UG-binding Proteins," *The Journal of Biological Chemistry*, Aug. 28, 1998, pp. 22819-22824, vol. 273, No. 35.
Laing et al., "A polymorphism of the CC16 gene is associated with an increased risk of asthma," *J. Med. Genet.*. vol. 35, pp. 463-467 (1998).
Laville et al., Nephrol Dial Transplant, 2004. 19:1947-1951.
Mandal, Asim K., et al. "Uteroglobin Inhibits Prostaglandin $F_{2\alpha}$ Receptor-mediated Expression of Genes Critical for the Production of Pro-inflammatory Lipid Mediators," *The Journal of Biological Chemistry*, vol. 280, No. 38, pp. 32897-32904, Sep. 23, 2005.
Mandal, Asim K., et al., "Uteroglobin Represses Allergen-induced Inflammatory Response by Blocking $PGD_2$ Receptor-mediated Functions," *The Journal of Experimental Medicine*, May 17, 2004, pp. 1317-1330, vol. 199, No. 10.
Mathis, et al., "Isolates of *Encephalitozoon cuniculi* from farmed blue foxes (*Alopex lagopus*) from Norway differ from isolates from Swiss domestic rabbits (*Oryctolagus cuniculus*)," *Parasitol Res.*, vol. 82, pp. 727-730 (1996).
Metzler et al., Nature Struc. Biol. 1997, 4:527-531.
Ngo et al., 1994, Protein Folding Problem and tertiary Structure Prediction, p. 492-295.
Nortier et al., "Proximal tubular injury in Chinese herb nephropathy: monitoring by neutral endopeptidase enzymuria," *Kidney International*, vol. 51, No. 1, pp. 288-293 (1997) (Abstract).
Skolnick et al., TIBS, 2000; 18(1):34-39.
Szelestei, et al., "Association of Uteroglobin Polymorphism with Rate of Progression in Patients with IgA Nephropathy," *American Journal of Kidney Diseases*, vol. 36, No. 3, pp. 468-473 (2000).
Yumane et al., "Bistable Electro-optical Fast Switching for Induced Smectic (Liquid Crystalline Polymer/Liquid Crystals) and (Pseudo Liquid Crystalline Copolymer/Liquid Crystals) Composite Systems," *Macromolecules*, vol. 30, pp. 3234-3241 (1997).
Zheng et al., "Uteroglobin is essential in preventing immunoglobulin A nephropathy in mice," *Nature Medicine*, vol. 5, No. 9, pp. 1018-1025 (1999).

* cited by examiner

*Primary Examiner* — Yunsoo Kim
(74) *Attorney, Agent, or Firm* — Klarquist Sparkman LLP

(57) ABSTRACT

Uteroglobin has been discovered to prevent IgA mediated diseases, such as IgA nephropathy, by preventing the deposition of IgA-Fibronectin immunocomplexes in tissues such as the renal glomeruli. The invention therefore includes methods of treating such diseases by administering therapeutically effective amounts of uteroglobin (and variants or mimetics) to prevent or improve the IgA mediated condition. Transgenic uteroglobin knockout animals, and animals in which uteroglobin-protein expression is reduced by antisense technology, also provide systems for studying IgA mediated diseases, and screening for appropriate treatments.

7 Claims, 6 Drawing Sheets

FIG. 1

```
Human CC10 kDa: 1 EICPSFQRVIETLLMDTPSSYEAAMELFSPDQDMREAGAQLKKLVDTLPQKPRESIKLMEKIAQSSLCN 70
                   ICP F  VIE LL   TPSSYE       F PD M  AG Q KK  D LPQ  RE I KL EKI   S LC
Rabbit Utg:        GICPRFAHVIENLLLGTPSSYETSLKEFEPDDTMKDAGMQMKKVLDSLPQTTRENIMKLTEKIVKSPLC ICP F  V E LL    S YEAA     F P D    AG QLX LVDTLPQ  R  I KL EKI   S LC
Rat CC10:          DICPGFLQVLEALLLGSESNYEAAALKPFNPASDLQNAGTQLKRLVDTLPQETRINIVKLTEKILTSPLCEQDLRV ICP F  V E LLM   S Y A     F P D    AG QLK LVDTLPQ  R  I KL EKI   S LC
Mouse CC10:        DICPGFLQVLEALLMESESGYVASLKPFNPGSDLQNAGTQLKRLVDTLPQETRINIMKLTEKILTSPLCKQDLRF
```

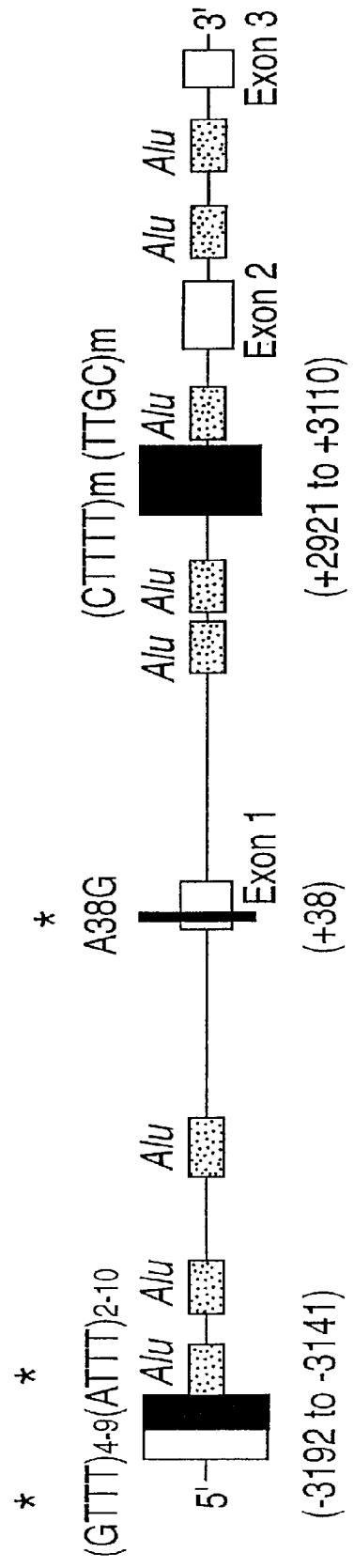

FIG. 5

UTEROGLOBIN IN THE TREATMENT OF IGA MEDIATED NEPHROPATHY

CROSS REFERENCE TO RELATED APPLICATIONS

This is a continuation of U.S. patent application Ser. No. 10/019,833, filed on Nov. 20, 2002, now abandoned which is a §371 U.S. national stage of PCT/US00/09979, filed Apr. 13, 2000, which was published in English under PCT Article 21(2), and claims the benefit of U.S. Application No. 60/130,434, filed Apr. 21, 1999, now expired, all of which are herein incorporated by reference in their entirety.

FIELD OF THE INVENTION

This invention concerns treatments for IgA mediated autoimmune disorders, such as IgA nephropathy.

GENERAL DISCUSSION OF THE BACKGROUND

Uteroglobin (UG) is a steroid-inducible protein that was originally discovered in the uterus of pregnant rabbits. Subsequently, this protein has been detected in many vertebrates, where it is widely expressed in tissues such as the thymus and pituitary glands, the respiratory and gastrointestinal tracts, and the pancreas, mammary gland, prostate, and seminal vesicle. This protein is known by several different names, including the progesterone binding protein, Clara cell 10-kd protein, urine protein-1, polychlorinated biphenyl-binding protein, and retinol-binding protein. According to PCT publication WO 98/53846, uteroglobin inhibits the activity of phospholipase $A_2$ ($PLA_2$), which plays critical roles in the inflammatory response.

Uteroglobin has also been reported to bind with fibronectin, and interfere with the deposition of fibronectin deposits in the renal glomeruli of knockout mice that are UG−/− (in which both copies of the uteroglobin gene are disrupted). Zhang et al., Science 276:1408-1412, 1997. However, others have reported that uteroglobin deficiency does not cause glomerular disease. Stipp et al., Am. J. Physiol. 271:L656-664, 1996; Reynolds et al., Am. J. Kidney Dis. 33:541-551, 1999. Hence the biological function of uteroglobin has been uncertain, and its role in particular diseases unknown.

The renal glomerulus is an anatomical unit of the kidney that is critical to its filtering function, and glomerulonephritis is a very diverse group of diseases that damage the glomerulus. Such glomerulopathies include poststreptococcal glomerulonephritis, rapidly progressive glomerulonephritis, focal glomerulonephritis, IgA nephropathy, minimal change disease, focal glomerulosclerosis, membranous glomerulonephritis, membranoproliferative glomerulonephritis (types 1, 2 and 3), mesangial proliferative glomerulonephritis, Goodpasture's syndrome, systemic lupus erythematosis, Wegener's granulomatosis, autoimmune thrombocytopenic purpura, and Henoch-Schonlein purpura. The cause, clinical features, treatment and prognosis of each of these conditions is distinct.

One of the most important and problematic of these glomerulopathies is IgA nephropathy, which is the most common primary renal glomerular disease throughout the world. IgA nephropathy causes an idiopathic renal hematuria with pathologic features that include elevated levels of circulating IgA-fibronectin complex, and granular deposition of IgA and C3 in a widened renal mesangium, with foci of segmental proliferative or necrotizing lesions. This disease often occurs following an upper respiratory infection, and available evidence suggests that nephropathy follows viral immunization of the mucosa (where IgA predominates). Abnormal production of IgA produces pathologic deposition of IgA in the kidneys. The ultimate cause of IgA nephropathy, however, has been elusive.

IgA nephropathy has been resistant to almost all types of treatment, and only responds modestly to corticosteroid therapy (which is much more effective against some other types of glomerulonephritis). The particular resistance of IgA nephropathy to treatment presents a serious public health problem. In some parts of the world, IgA nephropathy causes about 30% of all nephropathies, and nearly 50% of these patients develop end-stage renal disease. Such patients often require dialysis or renal transplantation, and have a high incidence of morbidity and mortality.

There is therefore a serious public health need for a treatment for IgA nephropathy, which has not been met by the previous disclosures in this field.

SUMMARY OF THE INVENTION

The present inventors have now surprisingly found that uteroglobin specifically helps prevent the development of IgA mediated diseases, such as IgA nephropathy. In the treatment of IgA nephropathy, the uteroglobin is believed to bind to fibronectin (Fn), and this prevents IgA-Fn complex formation and deposition of immune complexes in the kidney. Transgenic mammals (such as mice) that have a null allele for the uteroglobin gene (in which the gene has been structurally or functionally disrupted) have been found to develop IgA nephropathy. The development of IgA nephropathy in these animals can be inhibited or reversed by administering exogenous uteroglobin to the animal.

The invention therefore includes a method of preventing or treating IgA mediated autoimmune disorders, by identifying a subject having an IgA mediated autoimmune disorder, and administering to the subject a therapeutically effective amount of an agent selected from the group consisting of uteroglobin (including recombinant uteroglobin), or a fragment, derivative, mimetic, or variant thereof, which prevents or improves the IgA mediated autoimmune disorder. The IgA mediated disorder may be, for example, IgA nephropathy, Wegener's granulomatosus, Goodpasture's disease, or diabetic glomerulosclerosis. Several types of IgA nephropathy are included, such as IgA nephropathy due to hepatic cirrhosis, or pulmonary inflammation and fibrosis, or idiopathic IgA nephropathy. This treatment can be combined with other therapeutic interventions for these diseases, such as the administration of corticosteroids or cytotoxic agents.

The therapeutically effective variant of uteroglobin may be a peptide that has, for example, at least 85%, 90%, 95% or 98% homology to native uteroglobin. The present specification discloses several different species of uteroglobin (human, mouse, rat and rabbit) that illustrate variations in the amino acid sequence that retain the activity of uteroglobin and can be administered in accordance with this method. Alternatively, the production of endogenous uteroglobin can be stimulated to treat the IgA mediated disease.

The invention also includes a method of screening for a derivative, mimetic or variant of uteroglobin that prevents or treats an IgA mediated autoimmune disorder. Screening can be performed using a mammal (for example, a non-human mammal such as a mouse) having cells that normally express uteroglobin, wherein the cells have been altered to reduce or eliminate expression of uteroglobin, and predispose the mammal to develop the IgA mediated autoimmune disorder, such as IgA nephropathy. A test agent is then administered to the mammal, and it is determined whether the test agent interferes with development of the IgA mediated autoimmune disorder.

In particular embodiments, the cells of the mammal are altered by disrupting both alleles of a uteroglobin gene, for example by inserting a foreign nucleic acid sequence in the DNA sequence of each allele. Alternatively, the cells are altered by expression of an antisense nucleotide that reduces or eliminates expression of uteroglobin. The animals may then be used to screen for agents that inhibit development of the disease. Such animals provide a particularly convenient assay for screening for fragments, derivatives, mimetics, or variants of uteroglobin, which prevent or improve the IgA mediated autoimmune disorder.

An alternative screening test uses a cell or cellular extract that expresses a functional uteroglobin receptor. A test compound is contacted with the cell or cellular extract, to determine whether the test compound binds to the receptor with high affinity. Test agents that bind to the receptor with high affinity are then selected for further testing, for example using a transgenic mammal in which uteroglobin expression is disrupted.

The present invention also includes methods of predicting susceptibility to IgA nephropathy in a subject, by measuring a level of uteroglobin in a biological material from the subject (such as blood or urine), and determining if the uteroglobin level is below a normal level. Alternatively, a uteroglobin level below normal can also be used as a factor in diagnosing a suspected case of IgA nephropathy, either instead of or in addition to a renal biopsy. The abnormal uteroglobin level can also be used to help diagnose other IgA mediated diseases that are associated with abnormal uteroglobin expression.

Methods of diagnosis and screening for IgA mediated disease, such as IgA nephropathy, can also be performed by measuring levels of Uteroglobin-fibronectin (UG-Fn) or fibronectin-IgA (Fn-IgA) complexes. Now that it is known that uteroglobin is involved in the pathogenesis of IgA mediated diseases, it is also possible to detect mutations in the uteroglobin gene, or its receptor, to diagnose the diseases or a predisposition to them.

Methods are also disclosed for detecting a predisposition to developing asthma or an IgA mediated autoimmune disorder in a subject by obtaining a sample of nucleic acid from the subject, and screening for a polymorphism selected from the group consisting of: (a) an A-to-G polymorphism at position 38 in exon 1 of the uteroglobin gene; and (b) a polymorphism comprising a variation in a number of (GTTT) repeats between about bp −3200 and −3100.

Also disclosed are methods of treating pulmonary inflammation in a subject, by administering to the subject a therapeutically effective amount of an agent selected from the group consisting of uteroglobin, or a fragment, derivative, mimetic, or other variant thereof, which prevents or improves the pulmonary inflammation. The pulmonary inflammation can be pulmonary inflammation that accompanies an IgA mediated autoimmune disorder (such as Goodpasture's disease) or more general forms of pulmonary inflammation, such as the inflammation seen in asthma.

BRIEF DESCRIPTION OF THE FIGURES

FIG. 1 is a schematic drawing showing alignment of uteroglobin-like proteins (SEQ ID NO: 1, SEQ ID NO: 2, SEQ ID NO: 3 and SEQ ID NO: 4). For comparison, amino acid residues are shown above the primary sequences corresponding to residues found at the same position in the human protein (SEQ ID NO: 1). These sequences are predicted by translation of nucleotide sequences deposited with Genbank. These proteins are secreted proteins, and the N-terminal signal sequences, which are translated and processed off, have been edited out of this schematic comparison.

In FIG. 3A, equimolar concentrations of IgA and Fn were incubated at 37° C. for 2 hours in the absence and presence of uteroglobin. The IgA-Fn complex formation was quantitated by ELISA. Myoglobin was used as a non-specific control for uteroglobin. In FIG. 3B, $^{125}$I-IgA alone, or in combination with equimolar concentrations of Fn, was incubated at 4° C. for 2 hours with mesangial cells as described in Example 6. The graphs show significant uteroglobin mediated inhibition of binding of the IgA-Fn complex to the mesangial cells.

FIG. 4A, upper panel: Fn-mRNA levels in the glomeruli of UG−/− and UG+/+ mice; Lower panel: 1-Actin-mRNA, was used to standardize the Fn-mRNA levels.

FIG. 4B: Competitive PCR was used to determine the levels of α1-chain of type IV collagen, while FIG. 4C shows levels of PDGF-B-mRNA levels. Glomerular cDNAs from wild type (WT) (upper panel) and UG-knockout (lower panel) mice were competed with decreasing amounts of mutant (MT) cDNA. The MT-cDNA ranged from 0.1-2 μmol (lane 1-7) for α1-chain of type IV collagen and 0.0004-0.02 μmol for PDGF-B (lanes 1-7).

FIG. 4D illustrates induction of mesangial cell PDGF-B mRNA expression by IgA-Fn. Confluent mesangial cells in 6-well plates were incubated with DMEM/F-12+0.1% BSA for 24 hours. Some of the cultures were treated with 2 mg/ml of IgA+200 mg/ml of Fn that were preincubated at 37° C. for 2 hours to allow the generation of IgA-Fn complex. Others were incubated with 100 mg/ml Fn or PBS that served as controls. Total RNA was isolated from cells 4 hours after incubation. Upper panel: RT-PCR analyses of PDGF-B-mRNA levels; Lower panel: β-actin-mRNA expression was used to determine the quality and amount of RNA loaded. Lane 1, Control; Lane 2, Fn only; Lane 3, IgA only and Lane 4, IgA-Fn.

In FIGS. 4E and 4F, glomerular α-chain type IV collagen (E) and PDGF-B-mRNA (F) levels are compared between UG−/− and UG+/+ mice. *$P<0.05$.

FIG. 5 illustrates the molecular structure of the human uteroglobin gene, including the location of exons 1-3, and the A38G, (GTTT)m and (ATTT)n polymorphisms.

FIG. 6 shows molecular analysis of alleles for the A38G single nucleotide polymorphism.

DETAILED DESCRIPTION

Abbreviations

Figure 2:
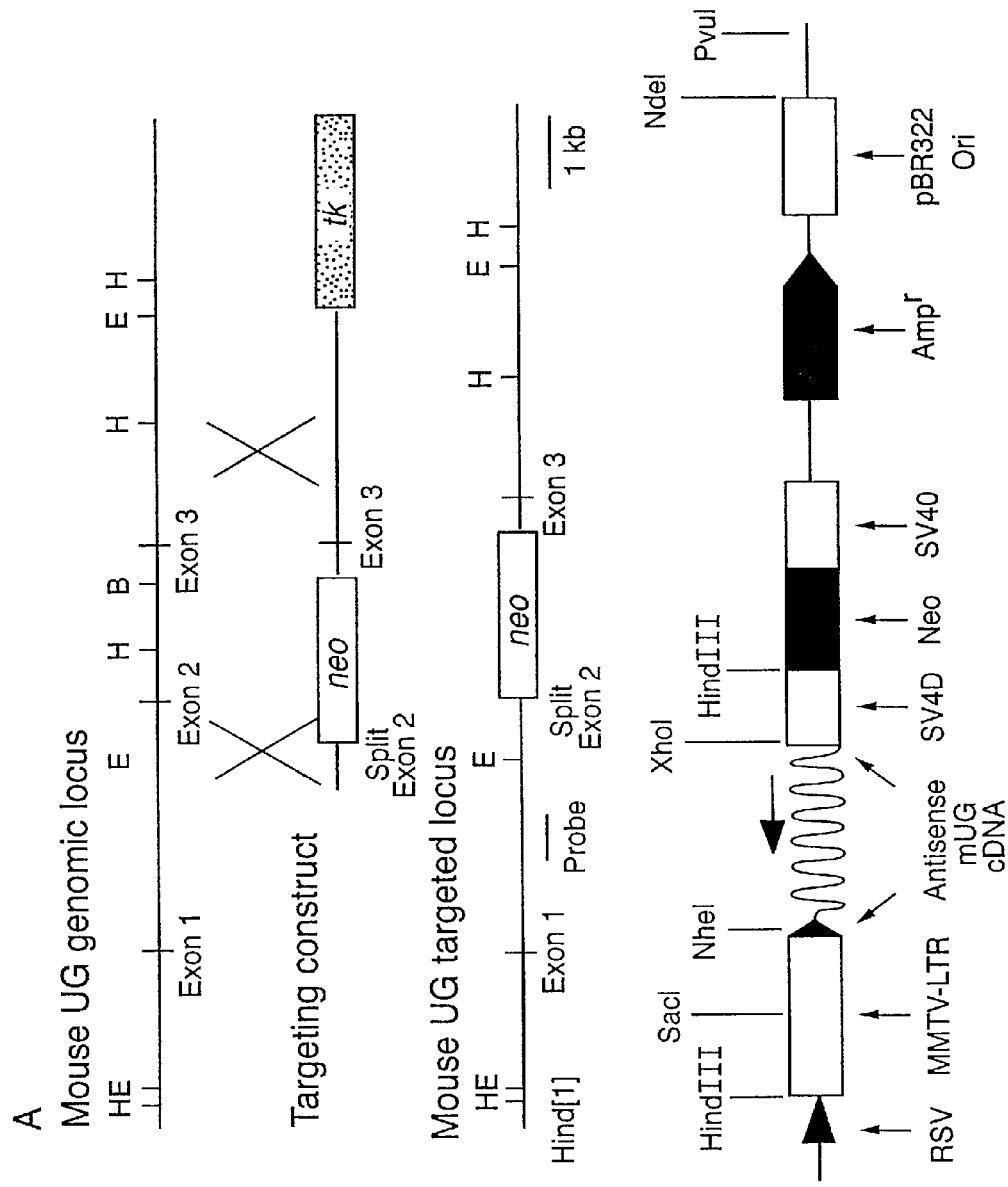
FIG. 2 shows the intended targeting construct of the transgenic uteroglobin knockout mouse; the restriction sites are B=BamIII, E=EcoRI, H=HindIII.

AS-UG: Antisense uteroglobin
IgAN: IgA nephropathy
KO: Knockout
UG: Uteroglobin

DEFINITIONS

Analog, derivative or mimetic: An analog is a peptide, or a peptide-like molecule, that differs in chemical structure from a parent compound, for example a homolog (differing by an increment in the chemical structure, such as a difference in the length of a peptide chain), a molecular fragment, a structure that differs by one or more functional groups, or a change in ionization. Structural analogs are often found using quantitative structure activity relationships (QSAR), with techniques such as those disclosed in *Remington: The Science and Practice of Pharmacology*, 19$^{th}$ Edition (1995), chapter 28. A derivative is a biologically active molecule derived from the base structure. A mimetic is a biomolecule that mimics the activity of another biologically active molecule. Biologically active molecules can include both chemical structures and peptides of protein entities that mimic the biological activities of the uteroglobin protein of the present invention.

Autoimmune disorder: A disorder in which the immune system produces autoantibodies to an endogenous antigen, with consequent injury to tissues.

cDNA (complementary DNA): a piece of DNA lacking internal, non-coding segments (introns) and regulatory sequences which determine transcription. cDNA is synthesized in the laboratory by reverse transcription from messenger RNA extracted from cells.

Deletion: the removal of a sequence of DNA, the regions on either side being joined together.

IgA: A secretory antibody found in the seromucous secretions of body tracts exposed to the external environment (such as saliva, tears, respiratory and gastrointestinal tract), where IgA provides an early antibacterial and antiviral defense. Serum levels of IgA can be qualitatively identified by immunoelectrophoresis, and can be quantitated by electroimmunodiffusion or radioimmunoassay. Normal serum levels of IgA are provided by individual laboratories where the test is performed.

Uteroglobin gene: a gene (DNA sequence) encoding the uteroglobin protein, the mutation of which is associated with the development of IgA nephropathy in transgenic (knockout) animals having a null allele (UG−/−). A mutation of the uteroglobin gene may include nucleotide sequence changes, additions or deletions, including deletion of large portions or all of the DLC-1 gene. The term "uteroglobin gene" is understood to include the various sequence polymorphisms and allelic variations that exist within the population. This term relates primarily to an isolated coding sequence, but can also include some or all of the flanking regulatory elements and/or intron sequences.

Uteroglobin cDNA: a mammalian complementary deoxyribonucleic acid (cDNA) molecule which, when transfected into cells, expresses the uteroglobin protein. The uteroglobin cDNA can be derived by reverse transcription from the mRNA encoded by the uteroglobin gene, and lacks internal non-coding segments and transcription regulatory sequences present in the uteroglobin gene.

Uteroglobin protein: the protein encoded by the uteroglobin cDNA, the altered expression or mutation of which can predispose to the development of certain IgA mediated immune disorders, such as IgA nephropathy. The uteroglobin protein is understood to include the species variations, and various sequence polymorphisms that exist, wherein amino acid substitutions in the protein sequence do not affect the essential functions of the protein.

Uteroglobin is a small globular homodimeric protein. It has a molecular weight of about 15.8 kDa, but it migrates in electrophoretic gels at a size corresponding to 10 kDa. It includes the human, rabbit, rat and mouse uteroglobin, as shown in PCT publication WO 98/53846. The 70 amino acid residues of the human uteroglobin sequence (SEQ ID NO: 1) are shown in FIG. 1, along with the uteroglobin sequences of the rabbit (SEQ ID NO: 2), rat SEQ ID NO: 3) and mouse (SEQ ID NO: 4).

Recombinant uteroglobin (rUG): Recombinant uteroglobin has substantially the same amino acid sequence as that of native uteroglobin protein from a particular species (such as human or mouse). An amino acid sequence having "substantially the same" amino acid sequence as that of the native human protein includes rUG having at least 75% sequence identity to the native protein, for example at least 85% identity or 95% or 98% identity.

Uteroglobin fragment: A "fragment" of uteroglobin refers to a portion of native UG amino acid sequence having six or more contiguous amino acid residues of the native protein sequence. The term "derivative" refers to peptide analogs of uteroglobin, including one or more amino acid substitutions and/or the addition of one or more chemical moieties, such as acylating agents or sulfonating agents, but wherein the derivative retains the biological activity of the parent molecule.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence. For example, a therapeutically effective oligonucleotide can be complementary to a MB1 encoding mRNA, or an MB1 encoding dsDNA.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference.

For purposes of the present invention, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

In vitro amplification: In vitro amplification can be performed by any method used to increase the copy number of a nucleic acid molecule. One appropriate technique for amplifying a nucleic acid molecule is the polymerase chain reaction (PCR). PCR is a technique in which cycles of denaturation, annealing with primer oligonucleotide, and extension with DNA polymerase are used to amplify (increase) the number of copies of a target DNA sequence.

Isolated: requires that the material be removed from its original environment. For example, a naturally occurring DNA or protein molecule present in a living animal is not isolated, but the same DNA or protein molecule, separated from some or all of the coexisting materials in the natural system, is isolated.

Oligonucleotide: A linear polynucleotide sequence of up to about 200 nucleotide bases in length, for example a polynucleotide (such as DNA or RNA) which is at least 6 nucleotides, for example at least 15, 50 or 100 nucleotides long.

ORF: open reading frame. Contains a series of nucleotide triplets (codons) coding for amino acids without any termination codons. These sequences are usually translatable into protein.

PCR: polymerase chain reaction. Describes a technique in which cycles of denaturation, annealing with primer, and then extension with DNA polymerase are used to amplify the number of copies of a target DNA sequence.

Pharmaceutically acceptable carriers: The pharmaceutically acceptable carriers useful in this invention are conventional. *Remington's Pharmaceutical Sciences,* by E. W. Martin, Mack Publishing Co., Easton, Pa., 15th Edition (1975), describes compositions and formulations suitable for pharmaceutical delivery of the proteins herein disclosed.

In general, the nature of the carrier will depend on the particular mode of administration being employed. For instance, parenteral formulations usually are injectable liquids that include pharmaceutically and physiologically acceptable carriers such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions can contain minor amounts of non-toxic auxiliary substances, such as wetting or emulsifying agents, preservatives, and pH buffering agents and the like, for example sodium acetate or sorbitan monolaurate.

The pharmaceutical compositions may also be administered as intranasal inhalants, for example in pharmaceutical aerosols utilizing solutions, suspensions, emulsions, powders and semisolid preparations of the type more fully described in *Remington: The Science and Practice of Pharmacy* ($19^{th}$ Edition, 1995) in chapter 95. A particular inhalant form is a metered dose inhalant containing the active ingredient, in a suspension or a dispersing agent (such as sorbitan trioleate, oleyl alcohol, oleic acid, or lecithin, and a propellant such as 12/11 or 12/114).

Probes and primers: Nucleic acid probes and primers may readily be prepared based on the nucleic acids provided by this invention. A probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (*Molecular Cloning: A Laboratory Manual*, Cold Spring Harbor, N.Y., 1989) and Ausubel et al. (*Current Protocols in Molecular Biology*, Greene Publishing Associates and Wiley-Intersciences, 1987).

Primers are short nucleic acids, for example DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al., Ausubel et al., and Innis et al., (*PCR Protocols, A Guide to Methods and Applications*, Innis et al. (eds.), Academic Press, Inc., San Diego, Calif., 1990). PCR primer pairs can be derived from a known sequence, for example, by using computer programs intended for that purpose such as Primer (Version 0.5,© 1991, Whitehead Institute for Biomedical Research, Cambridge, Mass.).

Purified: the term "purified" does not require absolute purity; rather, it is intended as a relative term. Thus, for example, a purified protein preparation is one in which the protein referred to is more pure than the protein in its natural environment within a cell. The term "substantially pure" refers to a purified protein having a purity of at least about 75%, for example 85%, 95% or 98%.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sequence identity: the similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Methods in Mol. Biol.* 24:307-31, 1988; Higgins and Sharp, *Gene* 73:237-44, 1988; Higgins and Sharp, *CABIOS* 5:151-3, 1989; Corpet et al., *Nuc. Acids Res.* 16:10881-90, 1988; Huang et al., *Comp. Appl. BioSci.* 8:155-65, 1992; and Pearson et al., *Meth. Mol. Biol.* 24:307-31, 1994

The NCBI Basic Local Alignment Search Tool (BLAST) (Altschul et al., *J. Mol. Biol.* 215:403-10, 1990) is available from several sources, including the National Center for Biological Information (NBCI, Bethesda, Md.) and on the Internet, for use in connection with the sequence analysis programs blastp, blastn, blastx, tblastn and tblastx. It can be accessed at the NCBI web site. A description of how to determine sequence identity using this program is available at the NCBI web site.

Variants or homologs of the uteroglobin protein are typically characterized by possession of at least 70% sequence identity counted over the full length alignment with the disclosed amino acid sequence using the NCBI Blast 2.0, gapped blastp set to default parameters. Such homologous peptides will more preferably possess at least 75%, more preferably at least 80% and still more preferably at least 90%, 95% or 98% sequence identity determined by this method. Sequence identity can be determined, in one instance, by aligning sequences and determining how many differences there are in the aligned sequence, and expressing these differences as a percentage. When less than the entire sequence is being compared for sequence identity, homologs will possess at least 75% and more preferably at least 85% and more preferably still at least 90%, 95% or 98% sequence identity over short windows of 10-20 amino acids. Methods for determining sequence identity over sequence windows are described at the NCBI web site. For comparisons of nucleic acid sequences of less than about 150 nucleic acids, the Blast 2 sequences function is employed using the default 0 BLOSUM62 matrix set to default parameters, (OPEN GAP 5, extension gap 2). Nucleic acid sequences with even greater similarity to the reference sequences will show increasing percentage identities when assessed by this method, such as at least 45%, 50%, 70%, 80%, 85%, 90%, 95% or 98% sequence identity.

One of skill in the art will appreciate that these sequence identity ranges are provided for guidance only; it is entirely possible that strongly significant homologs or other therapeutically effective variants could be obtained that fall outside of the ranges provided.

The present invention provides not only the peptide homologs that are described above, but also nucleic acid molecules that encode such homologs. One of ordinary skill in the art will appreciate that these sequence identity ranges are provided for guidance only; it is entirely possible that strongly significant homologs could be obtained that fall outside of the ranges provided. The present invention provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. ((1989) In *Molecular Cloning: A Laboratory Manual*, CSHL, New York) and Tijssen ((1993) *Laboratory Techniques in Biochemistry and Molecular Biology—Hybridization with Nucleic Acid Probes* Part I, Chapter 2, Elsevier, New York). Nucleic acid molecules that hybridize under stringent conditions to a human MB1 encoding sequence will typically hybridize to a probe based on either an entire human MB1 encoding sequence or selected portions of the encoding sequence under wash conditions of 2×SSC at 50° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Variant peptides: peptides having one or more amino acid substitutions, one or more amino acid deletions, and/or one or more amino acid insertions, so long as the peptide retains the property of inhibiting the development of IgA mediated autoimmune conditions such as IgA nephropathy. Conservative amino acid substitutions may be made in at least 1 position, for example 2, 3, 4, 5 or even 10 positions, as long as the peptide retains its activity, as readily measured by the assays disclosed in the present specification.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule is introduced into a host cell, thereby producing a transformed host cell. A vector may include nucleic acid sequences that permit it to replicate in a host cell, such as an origin of replication. A vector may also include one or more selectable marker genes and other genetic elements known in the art.

Mammal: This term includes both human and non-human mammals. Similarly, the term "subject" includes both human and veterinary subjects.

Animal: Living multicellular vertebrate organisms, a category which includes, for example, mammals and birds.

Transgenic Cell: transformed cells which contain foreign, non-native DNA. A transgenic animal is an animal containing a transgenic cell.

Amplify (amplifying, amplification): Increasing the concentration of a nucleic acid in a sample. One method will include the PCR reaction, which allows one to exponentially amplify the number of DNA molecules in a sample. Other methods may include, for example, dialysis.

Preventing or treating a disease: "Preventing" a disease refers to inhibiting the full development of a disease, for example in a person who is known to have a predisposition to a disease. An example of a person with a known predisposition is someone with a history of IgA nephropathy following an upper respiratory infection, or someone with a known mutation (for example in the uteroglobin gene) that may predispose to development of IgA nephropathy. "Treatment" refers to a therapeutic intervention that ameliorates a disease or pathological condition after it has begun to develop.

Therapeutically effective amount: An amount of a drug effective to inhibit or treat a disease. Although this amount varies depending on the severity and nature of a condition being treated, for human uteroglobin the amount administered to human adults may be, for example, 0.2 µg/kg to 500 mg/kg in single boluses, up to a total dose of several grams administered over several days.

Additional definitions of common terms in molecular biology may be found in Lewin, B. "Genes VII" published by Oxford University Press.

SEQUENCE LISTING

The amino acid sequences listed in the accompanying sequence listing are shown using standard three letter code for amino acids.

SEQ ID NO: 1 is a human uteroglobin amino acid sequence.
SEQ ID NO: 2 is a rabbit uteroglobin amino acid sequence.
SEQ ID NO: 3 is a rat uteroglobin amino acid sequence.
SEQ ID NO: 4 is a mouse uteroglobin amino acid sequence.
SEQ ID NOs: 5-17 are nucleic acid sequences of synthetic oligonucleotide primers.
SEQ ID NOs: 18-27 are amino acid sequences of uteroglobin polypeptide fragments.
SEQ ID NOs: 28-35 are nucleic acid sequences of synthetic oligonucleotide primers.

EXAMPLES

The invention is described in the following examples, which are intended to illustrate and not limit the invention.

Example 1

Construction of Uteroglobin Knockout Mouse

The development of non-human animal models in which a particular gene function has been eliminated has proven invaluable in the development and assessment of new therapeutic agents. Standard technologies may be utilized to produce a mouse or other animal model in which the function of the uteroglobin protein is eliminated or reduced. Such gene knockout models may be generated using the methods known in the art, including those described in U.S. Pat. Nos. 5,616,491 ("Knockout mice"), 5,714,667 ("Mice lacking expression of CTLA-4 receptor"), 5,569,824 ("Transgenic mice containing a disrupted p53 gene"), and 5,557,032 ("Knockout mice") and references cited therein.

In addition, transgenic non-human animal models overexpressing the uteroglobin protein, or variant or mutated versions of the protein, are useful for the assessment of agents, such as therapeutically effective variants of the protein. The mouse uteroglobin cDNA may be employed in conjunction with known methodologies for creating transgenic mice that over-express an introduced nucleic acid sequence to produce useful animal models. Suitable techniques for generating such transgenic animal models include those described in U.S. Pat. Nos. 5,489,742 ("Transgenic rats and animal models of inflammatory disease"), 5,489,743 ("Transgenic animal models for thrombocytopenia"), 5,304,489 (DNA sequences to target proteins to the mammary gland for efficient secretion), 5,476,995 ("Peptide production"), and 5,487,992 ("Cells and non-human organisms containing predetermined genomic modifications and positive-negative selection methods and vectors for making same"), and references cited therein.

In addition, conditional gene silencing (targeting) can be used to generate transgenic mice (for reviews see Porter, 1998, *Trends Genetics*, vol. 14; Rajewsky et al., 1996, *J. Clin. Invest.* 98:S51-S53). Conditional silencing of a gene allows cells to accumulate prior to the inactivation of the gene. The strategy of this method utilizes the bacteriophage-derived Cre-lox system. The Cre enzyme recognizes a sequence motif of 34 bp, called loxP. If a DNA segment is flanked by two loxP sites in the same orientation, Cre excises that segment from the DNA, leaving a single loxP site behind. Conditional targeting is accomplished by crossing responder mice, carrying the loxP flanked target gene, with regulator mice carrying the Cre transgene, which is expressed in a cell-type-specific or inducible manner.

The construction of a uteroglobin knockout mouse has been previously described in PCT publication WO 98/53846, which is incorporated by reference. A transgenic uteroglobin knockout (UG KO) mouse (in which the UG DNA sequence was disrupted by introduction of a heterologous DNA sequence into it) was created using those techniques. The UG KO mouse was created for the new purpose of studying uteroglobin as a specific treatment for IgA mediated autoimmune disorders, such as IgA nephropathy. The first step was to construct an appropriate DNA vector with which to target and interrupt the endogenous murine uteroglobin gene. The 3.2 kb BamHI-EcoRI DNA fragment containing exon 3 and flanking sequences of the uteroglobin gene from the 129/SVJ mouse strain were subcloned into the corresponding sites of the pPNW vector. A 0.9 kb fragment containing part of exon 2, and its upstream sequence, was amplified by PCR (with primers Primer-L (from Intron 1): 5'-TTC CAA GGC AGA ACA TTT GAG AC-3' (SEQ ID NO: 5); Primer-R (from Exon 2): 5'-TCT GAG CCA GGG TTG AAA GG C-3') (SEQ ID NO: 6) with NotI and XhoI restriction sites engineered into the termini for directional subcloning into the gene targeting vector. In this construct, 79 bp of exon 2 encoding 27 amino acids were deleted. The PCR fragment was placed upstream of the gene encoding neomycin resistance in pPNW, generating the gene targeting vector, pPNWUG. The vector is shown in FIG. 2, in which the PGK-neo cassette interrupts the uteroglobin gene, disrupting the protein coding sequence.

The pPNWUG gene targeting vector was linearized with NotI and electroporated into ES R' cells according to Nagy, A., et al. *Proc. Natl. Acad. Sci. USA* 90:8424 (1993). Ganciclovir and G-418 selection of the electroporated cells yielded 156 clones. Southern (DNA) blot analysis identified a 5.1 kb HindIII fragment of the wild-type uteroglobin allele and an additional 8.2 kb HindIII fragment resulting from homologous recombination in three out of the 156 clones. These ES R1 clones were injected into C57BL/6 blastocysts according to Capecchi, *Science* 244: 1288 (1989). Two different lines of mice, descended from different chimeric founders, were generated. Heterozygous offspring (UG+/−) carrying the targeted uteroglobin gene locus were mated and the genotypes of the progeny were analyzed by PCR.

Example 2

Verification of Uteroglobin Gene Knockout and Absence of Murine Uteroglobin Protein In order to verify that the homozygous knockout mice (UG−/−) did not possess any detectable murine uteroglobin (mUG), the uteroglobin gene-targeted mice were tested for expression of mUG-mRNA and mUG protein in several organs including the lungs. Total RNAs were isolated from different organs of UG+/+, UG+/−, and UG−/− mice. The reverse transcribed-polymerase chain reaction (RT-PCR) was used to detect mUG-mRNA. Target molecules were reverse transcribed using a mUG specific primer, mPr (5'-ATC TTG CTT ACA CAG AGG ACT TG-3') (SEQ ID NO: 7), and the cDNA generated was amplified using PCR primers mPr and mPl (5'-ATC GCC ATC ACA ATC ACT GT-3') (SEQ ID NO: 8). The PCR product was hybridized with an oligonucleotide probe, mPp (5'-ATC AGA GTC TGG TTA TGT GGC ATC C-3') (SEQ ID NO: 9) derived from exon-2 of the UG gene sequence. The primers and the probe used in mouse GAPDH RT-PCR are as follows: mGAPDH-r (5'-GGC ATC GAA GGT GGA AGA GT-3') (SEQ ID NO: 10); mGAPDH-1 (5'-ATG GCC TTC CGT GTT CCT AC-3') (SEQ ID NO: 11); mGAPDH-p (5'-GAA GGT GGT GAA GCA GGC ATC TGA GG-3) (SEQ ID NO: 12). The mUG-mRNA was detected in the lungs of UG+/+, and UG+/−, but not UG−/− mice. Similar data showed that mUG-mRNA is not present in either the prostate or uteri of UG−'/− mice, but is present in the mice with an intact uteroglobin gene.

Immunoprecipitation and Western blot analyses of mUG protein in the lungs yielded similar corroborative results. Tissue lysates from the kidneys, liver, and the lungs of the UG+/+ and UG−/− mice were prepared by homogenizing in a buffer (10 mM Tris-HCl, pH 7.5, 1% Triton X-100, 0.2% deoxycholate, 150 mM NaCl, 5 mM EDTA) containing 2 mM phenylmethylsulfonyl fluoride and 20 μg/mL each of aprotinin, leupeptin, and pepstatin A. The homogenates were centrifuged at 17,500×g for 30 minutes at 4° C. and immunoprecipitated as described (E. Harlow and D. Lane, Antibodies; a laboratory manual, 1st Ed. Cold Spring Harbor Laboratory Press, Cold Spring Harbor, N.Y., 1988) by incubating tissue lysates or plasma proteins (1 mg/mL) with rabbit antibody against murine Fn (1:100 dilution). Co-immunoprecipitation of purified murine fibronectin (Fn) and recombinant human uteroglobin (rhUG) (Mantile, et al., *J. Biol. Chem.* 267: 20343 (1993)) was performed by incubating equimolar concentrations of mFn with rhUG in the presence of 10% glycerol, 50 mM Tris-HCl, pH 7.5, 250 mM NaCl, 4.3 mM sodium phosphate at 4° C. for 1 hour, followed by adding anti-mFn: antibody (1:100 dilution). Equal amounts of extracted tissue proteins (30 μg) or immunoprecipitates were resolved either on 4-20% or 6% SDS-polyacrylamide gels under reducing conditions, followed by Western blotting with rabbit antibodies against either murine Fn (1:2000 dilution) or UG (1:2000 dilution). No mUG was detected in tissues or fluids from the UG−/− mice, while tissues from UG+/+ and UG+/− mice did contain the mUG protein.

Finally, histopathological analyses of the lungs of UG−/− mice lacked mUG specific immunostaining in bronchiolar epithelial cells, as described in WO 98/53846.

These three sets of results confirm that the homozygous uteroglobin knockout mouse, UG−/−, lacks mUG protein, or any detectable piece of the protein.

Example 3

Detection of IgA Glomerular Deposits by Fluorescence Microscopy

Using anti-IgA, IgG and IgM-antibodies, immunofluorescence analysis was performed on frozen or partially protease-digested, paraffin-embedded sections of the kidneys from UG−/−, UG+/− and UG+/+ littermates.

Uteroglobin (UG) deficient mice (−/−) were generated and genotyped as previously described in Example 1. The UG−/−, UG+/−, and UG+/+ mice were euthanized, their kidneys were perfused with phosphate buffer solution (PBS), and frozen sections were prepared. Sections were incubated with fluorescein isothiocyanate (FITC)-conjugated goat anti-mouse immunoglobulin (Ig) A, anti-mouse IgM, anti-mouse-IgG or anti-mouse complement C3. Epifluorescence was examined and photographed with a Zeiss Axiophot microscope.

While the glomeruli of UG−/− and UG+/− mice accumulated heavy and moderate deposits of IgA, respectively, IgA deposits were undetectable in the glomeruli of the UG+/+ littermates. Moreover, none of these animals manifested detectable IgG or IgM-immunocomplexes.

Example 4

Knockout Mice Manifested Pathologic Features of IgA Nephropathy (IgAN)

The characteristic pathologic features of human IgAN include hematuria, high levels of circulating IgA-Fn complex, and abnormal deposition of IgA, Fn and collagen in the renal glomeruli. Light microscopic examination of the urine revealed that the UG-knockout mice manifested significant hematuria, with the erythrocyte count in the urine of the UG−/− mice (>200 red cells per high power field) being strikingly higher than that in the urine of the UG+/+ littermates (0-5 cell per high power field). The abnormal deposition of Fn and collagen in the glomeruli of UG-knockout mice, together with the presence of massive IgA-deposition and hematuria, establish pathologic findings consistent with human IgAN.

Example 5

Circulating IgA Complex Levels Elevated

In addition to the abnormal deposition of IgA in the glomeruli, patients suffering from IgAN usually manifest high levels of circulating IgA-Fn complex. Cederholm et al, *Proc. Natl. Acad. Sci. USA* 83:6151, 1986; and *Proc. Natl. Acad. Sci. USA* 85:4865, 1988; Jennette, et al., *Am. J. Kid. Dis.* 18:466, 1991; Hollingsworth et al., *J. Am. Soc. Nephrol.* 1:565, 1990; Baldree et al., *Am. J. Kid. Dis.* 22:1, 1993. An elevated level of IgA-Fn complex was detected in the plasma of the UG−/− mice by an enzyme linked immunosorbent assay (ELISA).

Plasma levels of IgA were measured by a modification of the sandwich enzyme-linked immunosorbent assay (ELISA) described previously by Klein-Schneegans et al, *J. Immunol. Methods* 119:117, 1989. Polystyrene microtiter plates were coated with goat anti-mouse IgA antibody. After blocking the plates with bovine serum albumin, the plasma samples were applied at 1:100 dilutions. After incubation, alkaline phosphatase conjugated goat anti-mouse IgA antibody (1:500) was added and incubated for 60 minutes. The color was developed by the addition of p-nitrophenyl phosphate solution and measured at 405 nm. The standard curve was set up by the reaction with different concentrations of purified mouse serum IgA. Plasma IgA-Fn levels were measured by the same procedure except that polystyrene microtiter plates were coated with rabbit anti-mouse Fn antibody.

While the plasma of control mice contained a very low level of IgA-Fn complex, the levels of this complex in the plasma of UG-knockout mice (UG−/−) are significantly ($p<0.05$) higher (Table 1). Compared with the wild type littermates, no apparent elevation of IgA level in the plasma of UG-knockout mice was observed (Table 1). Taken together with the findings that UG-knockout mice manifest heavy deposits of IgA and Fn in the glomeruli, and the presence of high levels of IgA-Fn complex in the plasma of these mice as well as in those of the IgAN patients, the elevated plasma level of the IgA-Fn complex is a harbinger of abnormal glomerular IgA and Fn deposition. These results also indicate that the pathological findings in UG-knockout mice are very similar, if not identical, to those reported in human IgAN.

TABLE 1

Comparison of Plasma IgA and IgA-Fn in UG+/+ and UG −/− Mice

| Genotype | No. Mice | Plasma IgA (mg/dL) | Plasma IgA-Fn* |
|---|---|---|---|
| UG+/+ | 4 | 7.38 + 1.22 | 0.026 + 0.016 |
| UG−/− | 4 | 12.08 + 1.71 | 0.619 + 0.141 |

The levels of plasma IgA-Fn complex between UG+/+ and UG−/− mice are significant at p < 0.05.
*The relative levels of IgA-Fn complex are expressed as O.D. obtained from the ELISA.

These results therefore provide an example of a diagnostic or screening test that can be performed to help determine whether an animal (such as a mammal) has an IgA mediated disease, such as an IgA mediated nephropathy. The much lower plasma IgA-Fn levels in the UG−/− mice (more than 20 times less than in UG+/+ mice) and the increase in plasma IgA (a 60% increase) can be used to diagnose IgA nephropathy. The specific elevations observed in this experiment are not intended to limit the diagnostic or screening method, but instead are examples of specific elevations that are associated with the development of IgA nephropathy in one species. These values were determined in mice, but the same principles can be used in any species, such as humans, where species specific values can be obtained. The normal and abnormal values can be obtained in persons who are diagnosed (by conventional clinical techniques) as having an IgA nephropathy. The predictability of these values can be further enhanced by measuring uteroglobin levels, or performing genotypic analysis of the uteroglobin gene, to confirm the presence of abnormal uteroglobin expression in the subject.

It is believed that an increase of plasma IgA level of at least 25%, and/or an increase in IgA-Fn by a factor of at least 5 or 10 times above normal, may be taken to indicate early IgA mediated disease, such as IgA nephropathy.

Example 6

Uteroglobin Interferes with IgA-Fn Binding

The results in Example 5 show that uteroglobin interferes with IgA-Fn interaction, thereby averting glomerular deposition of both IgA and Fn. Example 6 further demonstrates that uteroglobin can be supplied to interfere with IgA-Fn complex-formation. A 160 mg amount of IgA was incubated with 80 mg Fn in 1 ml PBS solution in the presence or absence of different concentrations of UG (2-4 mg/ml) at room temperature for 2 hours. The formation of IgA-Fn complex was determined by ELISA as described above. The specificity of the measurement was tested by the addition of IgA or Fn alone to the anti-Fn antibody or anti-IgA antibody coated wells.

Figure 3A:
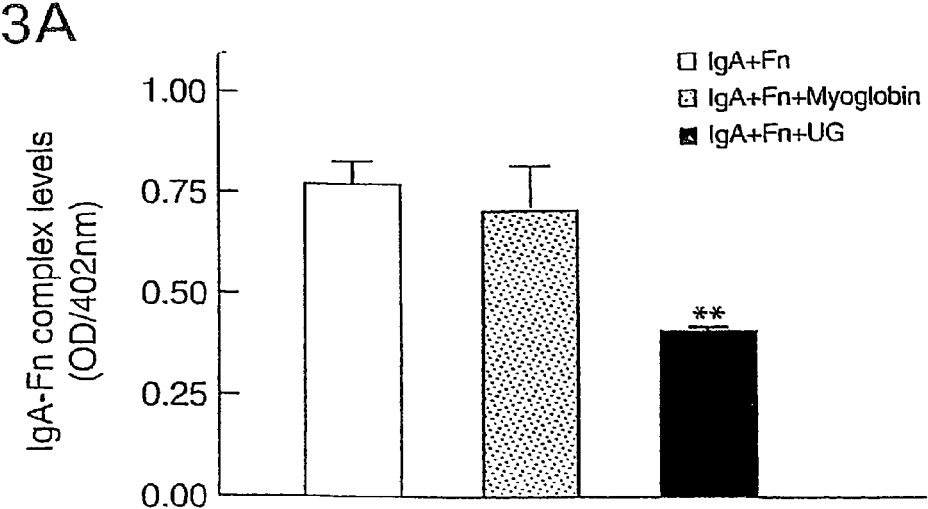
FIGS. 3A and 3B are graphs illustrating uteroglobin inhibition of IgA-Fn complex formation and IgA-Fn complex binding to cultured mesangial cells.

The results shown in FIG. 3A demonstrate that UG prevents the formation of IgA-Fn complex (FIG. 3A), even though UG itself does not bind with IgA (data not shown). A non-specific protein, myoglobin, showed no such effect (FIG. 3A). Hence UG plays an essential role in suppressing IgA-Fn complex-formation, and is consequently a potent inhibitor of IgA-deposition in the glomeruli. This assay can also be used as a convenient technique to screen uteroglobin variants (including fragments) for therapeutic activity.

It has been reported that IgA binds with the renal mesangial cells, and such binding is enhanced in IgAN patients. Moreover, IgA binding has been reported to activate the renal mesangial cells in vitro. Thus, it was determined whether the IgA-Fn complex also binds with mesangial cells, and whether UG interferes with this binding. Binding studies were carried out using $^{125}$I-IgA, $^{125}$I-IgA-Fn complex, and cultured mesangial cells.

In the binding studies, 50 mg of mouse serum IgA was radioiodinated using sodium [$^{125}$I] iodide (2 mci, carrier free) and Iodo-BEADS. The reaction was carried out in 130 µl of PBS, pH 7.4 at 25° C. for 10 minutes and $^{125}$I IgA was purified by sephadex G50 column. The specific activity of purified carrier-free $^{125}$I IgA was 10.6 mCi/mg. To produce IgA-Fn complex, different amounts of $^{125}$I IgA were mixed with equal molar amounts of Fn in the absence and presence of equimolar amounts of UG at room temperature for 2 hours. Human mesangial cells (HMC) were cultured as previously described. For the binding study, the confluent HMC in a 48-well plate were incubated with DMEM/F12 medium with 0.1% BSA for 24 hours, and then washed once with cold Hank's balanced salt solution (HBSS). Cells were incubated with varying concentrations of $^{125}$I IgA, $^{125}$I IgA-Fn, or $^{125}$I IgA-Fn-UG in 0.5 ml HBSS, pH 7.6, containing 0.2% BSA at 40° C. for 2 hours. The binding was stopped by rapid removal of unbound $^{125}$I IgA, and cells were washed three times with HBSS and solubilized in 1N NaOH. The radioactivity was measured by a gamma counter.

Figure 3B:
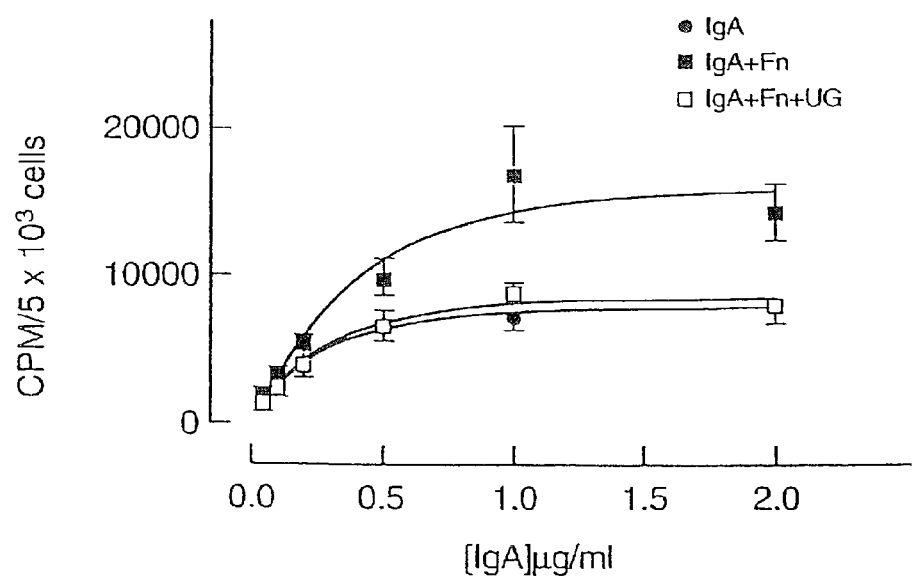
Figure 4:
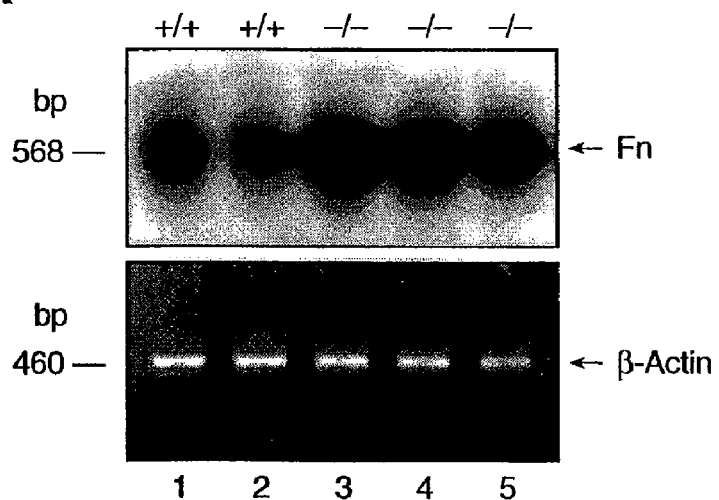
FIG. 4 is a series of gels and graphs which show differential expression of several proteins in UG−/− mice, as compared to UG+/+ mice.
Figure 4:
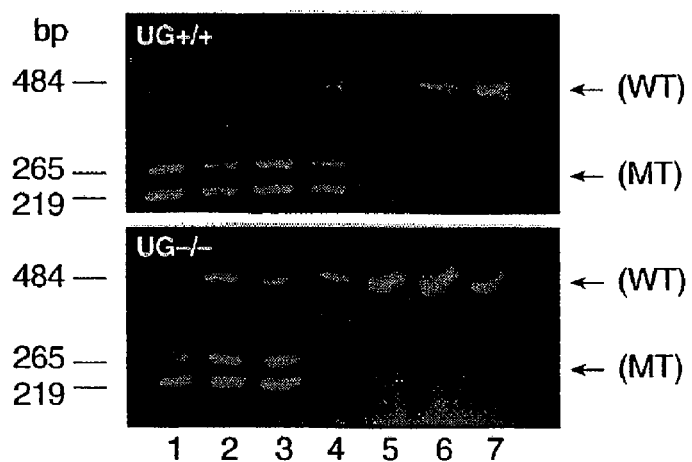
Figure 4:
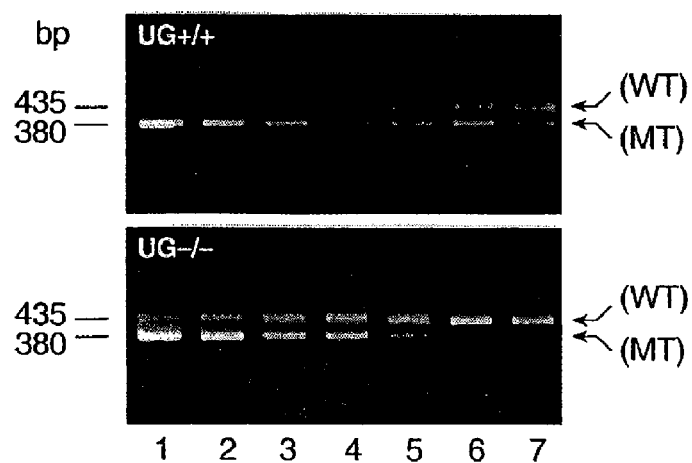
Figure 4:
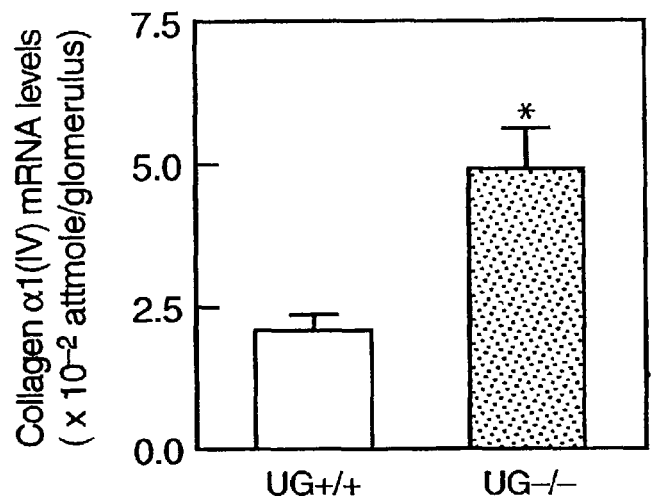
Figure 4:
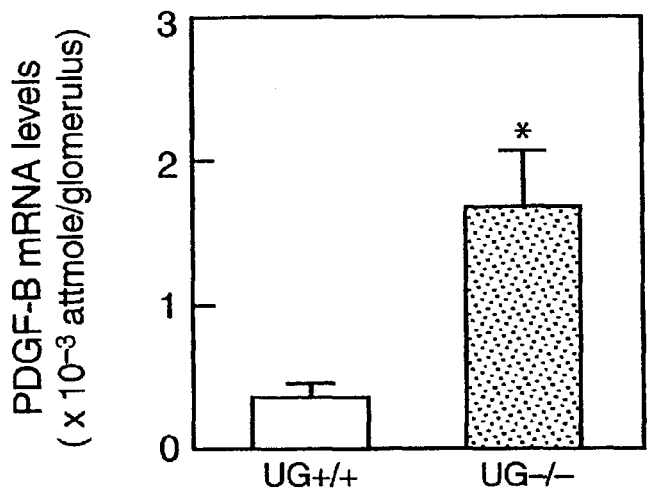
Figure 4:
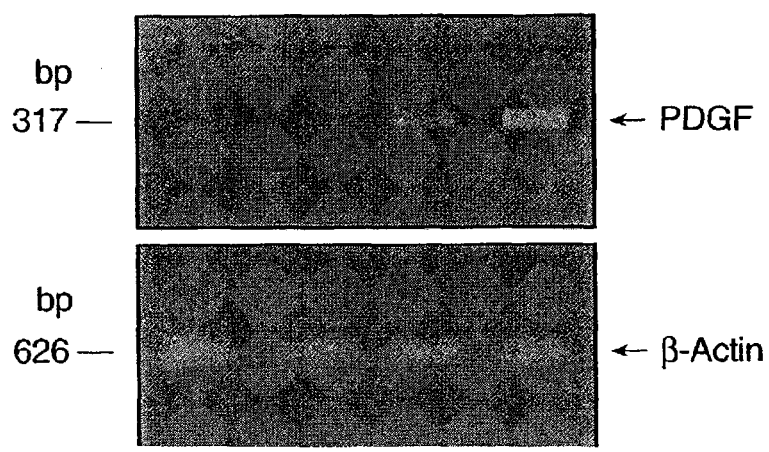

The results (FIG. 3B) show that while both IgA as well as IgA-Fn bind with these cells, the level of binding is much higher for IgA-Fn compared with IgA alone. More importantly, in the presence of UG, the level of $^{125}$I-IgA-Fn binding was significantly reduced. These results indicate that UG competes with IgA-Fn complex for binding with the cells, or that UG disrupts the IgA-Fn complex formation by its high-affinity binding with Fn to form Fn-UG heteromers. Once again, this assay would be suitable for screening uteroglobin variants for biological/therapeutic activity.

To determine whether UG prevents the glomerular deposition of exogenous IgA in vivo, UG−/−, UG+/− and UG+/+ littermates were injected intra-arterially with fluorescein isothiocynate (FITC)-conjugated IgA in the presence or absence of UG.

The mice were anesthesized, a polyethylene tube was inserted into the left carotid artery, and 100 mg FITC-conjugated human serum IgA with or without 100 mg UG was injected. Mice injected with IgA with myoglobin (Sigma) or FITC (Sigma) alone served as controls. The mice were sacrificed 6 hours after injection. The accumulation of FITC-conjugated IgA was shown under fluorescence microscopy. Intra-arterial, as opposed to intravenous, route of administration was chosen to minimize the degradation of FITC-IgA during its passage through the liver. The results showed a strong immunofluorescence in the glomeruli of the UG−/− mice that received FITC-IgA alone, but virtually no such accumulation was detected when a mixture of FITC-IgA and UG was administered. Myoglobin, used as a non-specific control, failed to provide any protection against FITC-IgA accumulation in the glomeruli of these mice. Compared with the glomeruli of the UG−/− mice, those of the wild type littermates manifested a total lack of immunofluorescence.

Even when a higher dosage (300 µg) of FITC-IgA was injected into the UG+/+ mice, they showed no detectable glomerular accumulation (data not shown) suggesting a higher threshold for abnormal glomerular IgA-accumulation in these mice. No detectable accumulation of fluorescence was found in the glomeruli of these animals. These results demonstrate that UG has a critical in vivo function in preventing the glomerular IgA-accumulation. This assay also provides yet another screening technique for selecting UG variants that would interfere with IgA-Fn deposition in the glomeruli.

Example 7

Protein Deposition in Isolated Glomeruli To determine the molecular mechanism(s) of IgAN in the UG-knockout mice in further detail, pure populations of glomeruli were isolated from the kidneys of UG+/+ and UG−/− mice by micro-dissection, and evaluated for the level of expression of Fn and α-chain-specific type IV collagen within this organelle. Glomeruli from the kidneys of UG−/−, UG+/−, and UG+/+ mice were isolated by microdissection as previously described [Zheng et al., Kid. Int. 54:1999 (1998); Yang, et al., *J. Am. Soc. Nephrol.* 5:1610 (1995); Peten et al., *Am. J. Physiol.* 263, F951 (1992)]. Total RNA was extracted from glomeruli and reverse transcribed with oligo-dT. Glomerular fibronectin (Fn) mRNA levels were assessed by semi-quantitative RT-PCR using the Fn-primers [Bergijk, et al., *J. Pathol.* 178:462 (1996)] as follows: Fn-L:AGA AGC CTG GAT CCC CTC CC (SEQ ID NO: 13); Fn-R:TGG AAC GGC GTC CAA GAG ATG (SEQ ID NO: 14) and probe, Fn-P: GGT GTC ACG GAG GCC ACC ATT ACT G (SEQ ID NO: 15). The β-actin mRNA levels were determined at the same time. Corresponding PCR products were 568 bp for Fn, and 460 bp for β-actin, respectively. Glomerular glyceraldehyde phosphate dehydrogenase (GAPDH), PDGF-B, α-chain of type IV collagen-mRNA levels were measured by competitive PCR. The methods, primers, and mutant templates used for glomerular GAPDH, PDGF-B, and α-1 type IV collagen competitive PCR were described previously.

The Fn-mRNA levels were determined by semi-quantitative RT-PCR, and the results show that these levels are significantly higher in the glomeruli of UG−/− compared with those of the UG+/+ littermates (FIG. 4A). In addition to the accumulation of Fn and IgA, the glomeruli of IgAN-patients as well as those of the UG-knockout mice show abnormal deposition of collagen. The accumulated collagen in the glomeruli has been reported to be of type IV. The level of α-chain-specific type IV collagen-mRNA from the glomeruli isolated from UG−/− and UG+/+ mice was determined by quantitative RT-PCR. The results (FIGS. 4B and 4E) show that type IV collagen-mRNA is expressed at a much higher level in the glomeruli of UG−/− mice compared with that in the glomeruli of UG+/+ mice.

Since PDGF and TGFβ are known stimulators of Fn- and collagen production in glomerular cells, the PDGF and TGFβ-mRNA levels were also determined in isolated glomeruli from UG−/− and UG+/+ littermates by competitive RT-PCR. The results (FIGS. 4C and 4F) show that PDGF-mRNA is expressed at a strikingly higher level in the glomeruli of UG−/− mice compared with the glomeruli of the UG+/+ littermates (FIGS. 4C and 4F), while the glomerular TGFβ1-mRNA levels remained unchanged (data not shown). These findings in UG-knockout mice are in agreement with those reported in human IgAN patients.

To determine if IgA or IgA-Fn complex stimulates PDGF-mRNA production in the glomerular mesangial cells, in vitro experiments were performed in which cultured human glomerular mesangial cells were stimulated with IgA, IgA+Fn and Fn alone, and the level of PDGF-mRNA was measured. IgA-Fn complex was formed in vitro by incubation of 2 mg/ml IgA with 200 mg/ml Fn in PBS solution at 37° C. for 2 hours. To examine the effect of IgA-FN on the expression of PDGF-B by HMC, the confluent HMC in 6-well plates were incubated with DMEM/F12 medium with 0.1% BSA for 24 hours and then washed once with HBSS. Cells were incubated with 2 mg/ml IgA, IgA-Fn, or the same volume (500 μl) of Dulbecco's PBS (Life Technologies, Gaithersburg, Md.). Total RNA was extracted from cells after 4 hours, 6 hours, 12 hours and 24 hours of treatment, and reverse transcribed with oligo-dT. The semi-quantitative RT-PCRs were performed using human PDGF-B primers as previously described [Shaddy, et al., *Biochem. Mol. Med.* 57:10 (1996)]. Results from these studies are shown in FIG. 4D, wherein lane 1 is a control; lane 2 is treatment with Fn only; lane 3 is treatment with IgA only; and lane 4 is treatment with IgA-Fn.

The results showed that the cells treated with IgA alone (FIG. 4D, lane 3) had a low level of PDGF-mRNA expression, while treatment with IgA+Fn (lane 4) caused a highly elevated level of expression, although Fn alone (lane 2) did not show such an effect. Hence while IgA alone may cause a small increase in PDGF-mRNA in mesangial cells, high levels of the IgA-Fn complex, found in the plasma of IgAN patients and in that of the UG-knockout mice, in turn appears to induce an even higher level of PDGF-mRNA. Consequently, in the glomeruli of IgAN patients, higher levels of Fn and collagen type IV expression would be expected. This is believed to initiate a cycle causing abnormal glomerular accumulation of IgA, Fn and collagen, characteristic of IgAN.

Since UG interferes with IgA-Fn complex formation but does not bind IgA, it is reasonable to expect a small elevation of PDGF-mRNA production by mesangial cells treated with IgA alone (FIG. 4D, lane 3). Although not wishing to be bound by theory, it is proposed that uteroglobin prevents the development and progression of IgAN by the following mechanism. Under normal physiological conditions, there is a balance among the levels of circulating UG, IgA and Fn. Uteroglobin binds Fn with high-affinity, forming Fn-UG heteromers, which prevents not only Fn self-aggregation, essential for abnormal tissue-deposition, but also counteracts the formation of IgA-Fn complexes, found in the plasma of IgAN patients. However, in pathological conditions, such as inflammation of the airways, UG production and its circulating levels are suppressed. As a result, the balance between Fn-UG, and Fn-IgA are disrupted, allowing free Fn to form IgA-Fn and Fn-Fn complexes more readily Suppression of UG production may also allow the IgA and IgA-Fn complexes to bind to the mesangial cells, to stimulate PDGF production. The interaction of PDGF with its receptor on mesangial cells causes enhanced Fn and collagen-production. Since Fn also binds collagen, the glomeruli of IgAN patients accumulate IgA, Fn, and collagen.

This hypothesis is consistent with the observation that inflammation in the lung, a major source of plasma UG, can lead to the development of IgAN. Moreover, 60% of the IgAN patients that undergo renal transplantation have recurrence of the disease, and these patients also manifest high levels of plasma IgA-Fn complex.

Using this model, it is now possible to perform further detailed analyses on the molecular mechanism(s) of IgAN, and test novel therapeutic approaches, including the use of recombinant human UG, to treat IgA mediated diseases, such as IgA nephropathy.

Example 8

Use of Uteroglobin Antisense Oligonucleotides

It has been reported that during the use of conventional gene-targeting methods, disruption of unrelated genes flanking the intended target-loci may occur, and result in phenotypic differences from targeted-disruption of an identical gene. This example uses antisense technology to confirm that the phenotype of the UG gene knockout mice is in fact caused by a disruption of the UG gene, and not unrelated genes flanking the uteroglobin gene sequence. This example also illustrates how antisense technology can be used to functionally disrupt expression of the UG gene in a mammal, to provide a system for studying and developing new drugs for treating IgA mediated diseases.

The antisense strategy disclosed in this example suppressed UG-protein production without physical disruption of the endogenous UG gene. Transgenic mice were generated that expressed UG antisense-RNA to suppress UG-protein production. The phenotype of two independently derived lines of UG-antisense transgenic (UG-AS) mice, is virtually identical to those of the heterozygous UG-knockout (UG+/−) mice. These results confirm that abnormal fibronectin (Fn) and collagen deposition, in the renal glomeruli of the UG knockout mice, are caused by the lack of UG-protein, and are not due to the disruption of an unrelated gene flanking the UG locus.

Rabbit anti-mouse Fn-antibody was obtained from Life Technologies (Gaithersburg, Md.) and FITC-conjugated goat and rabbit IgG was purchased from Cappel Laboratories (West Chester, Pa.). All animals used in this study were housed under 10 hour dark and 14 hour light cycles. In order to generate the antisense transgene construct, a full length mouse UG (mUG)-cDNA (Ray et al., *Biochem Biophys Res Commun.* 197:163-171, 1993) was subcloned in the antisense orientation (AS-UG) between NheI and Xho I sites of the eukaryotic expression vector pMAMneo (Clontech, CA). The 1.2 kb linearized HindIII-NdeI (AS-UG) fragment was microinjected into single cell B6XSJL embryos (DNX, Inc.) which were then inserted into the oviducts of pseudopregnant surrogate CD1 mice (DNX, Inc). Transgenic mice were identified by Southern hybridization analysis of BamH1-digested mouse genomic DNA using UG-cDNA probe. Simultaneously, mice were also genotyped by PCR amplification using mUG cDNA-specific primers (mUG-L: 5'-ATGAAACTCGCTGTCACCC-3') (SEQ ID NO: 16); mUG-R: 5'-TACACAGTGAGCTTTGGGC-3') (SEQ ID NO: 17). PCR amplification was carried out with an initial denaturation at 94° C. for 1 minute; 30 cycles of 94° C. for 1 minute, 60° C. for 1 minute, and 72° C. for 1 minute.

Total RNA was isolated from freshly collected lungs, prostate and uterus according to Chomczynski and Sacchi (*Anal Biochem* 162:156-159, 1987). The RNAs were analysed by RT-PCR. Two hundred nanograms of total RNA were used for the reverse transcription and PCR amplification using GenAmp RT-PCR kit (Perkin Elmer) and primers mUG-L and mUG-R to reverse-transcribe antisense and sense RNAs respectively. The amplified cDNA fragments were resolved by electrophoresis on agarose gels, transferred to nylon membranes, and probed with 32P-labeled mUG cDNA probe and autoradiography.

Tissues from UG-transgenic and wild type littermates were homogenized in 10 mM Tris-HCl at pH 7.5 and in 10 mM EDTA. 2 mM phenylmethylsulfonyl fluoride and 20 µg/ml each of aprotinin and leupeptin, respectively. The tissue homogenates were then centrifuged at 17,500×g for 30 minutes at 4° C., and the supernatants were mixed with one volume of 2× non-reducing SDS-PAGE sample buffer and boiled. Equal amounts (30 µg) of total protein from the homogenates were loaded and subjected to electrophoresis using a 4-20% gradient polyacrylamide gel (Bio-Rad). The protein bands were electrotransfered to a nitrocellulose membrane (Schleicher and Schuell). The membrane was blocked, washed with PBS-T (PBS containing 0.1% Tween 20), and incubated with goat anti-hUG antibody (1:500 dilution). The protein bands reacting to this antibody were visualized by using a Kodak BioMax chemiluminescent detection kit according to the manufacturer's instructions.

For histopathology and immunohistochemistry studies, kidneys from control and transgenic mice were fixed in neutral-buffered 4% formalin, embedded in paraffin and sectioned at 4-6 µm. They were stained with hematoxylin and eosin (H & E). For detecting fibronectin in the renal glomeruli, an immunofluorescence technique was used as previously described in Zhang et al., *Science* 276:1408-1412, 1997. The goat anti-murine fibronectin antibody was purchased from Santa Cruz Biotechnology (Cat#sc-6953) and fluoroceinisothiocynate (FITC)-conjugated rabbit and-goat IgG was obtained from Cappel Laboratories. In a separate set of experiments, kidneys were also stained by Masson's trichrome method for collagen detection.

Goat FITC conjugated anti-mouse immunoglobulin A (IgA) (α-chain-specific) antibody was purchased from Sigma (St. Louis, Mo.). The procedure for immunofluorescence to detect IgA immunocomplexes was performed according to Howie et al. (*J. Clin. Pathol.* 43:257-259, 1990) with minor modifications. Briefly, the dewaxed tissue sections were treated with 0.1% trypsin at 37° C. for 6 minutes. The digestion was stopped by removal of trypsin and by incubation with 10% goat serum for 10 minutes. The slides were washed four times (15 min each) with PBS and incubated with goat FITC-conjugated anti-mouse IgA (1:2) at 37° C. for 45 minutes. The slides were washed, coverslipped, examined under epifluorescence, and photographed as described above.

Mice expressing antisense UG-RNA were generated using the full length murine UG-cDNA in its antisense orientation downstream of the MMTV-LTR promoter of the eukaryotic expression vector pMAMneo. Four founder mice were obtained, two of which were bred to C57BL/6J mice and two independent transgenic mouse lines were established. The transgenic mice were identified by both Southern blot and PCR analyses, which confirmed the genomic integration and germline transmission of the transgene to the progeny of both founders. A 262 bp DNA-fragment was detected after PCR amplification of the genomic DNA of the AS-UG mice, but not from the endogenous UG gene.

Expression of the UG-sense and antisense-RNA and UG-protein in AS-UG mice was detected by isolating total RNA from the lungs and the uterus and analyzing them by Northern blotting. The results showed that both UG-sense and antisense RNAs are expressed in these organs. To determine whether the UG-protein expression was suppressed as a result of UG antisense RNA expression, Western blot analysis of the tissue homogenates was performed using anti-UG antiserum. The results showed that the intensity of the UG-protein bands derived from the lungs and uteri of AS-UG mice are drastically reduced compared with those of the wild type controls.

AS-UG mice manifest abnormal deposition of fibronectin and collagen in the renal glomeruli, just like the homozygous (UG−/−) and heterozygous (UG+/−) mice generated by targeted disruption of the UG gene in transgenic mice. Like the heterozygous UG-knockout mice, the AS-UG mice had no weight loss or early mortality. Compared with the results of histopathological analyses using H & E staining of the kidneys, the wild type littermates showed no abnormalities, while an abnormal deposition of an eosinophilic material was readily detectable in the glomeruli of AS-UG kidneys.

Immunofluorescence analysis of the kidneys with Fn-antibody showed that while Fn-specific immunofluorescence in the renal glomeruli of wild type littermates is totally lacking, it was readily detectable in the glomeruli of AS-UG glomeruli. Moreover, Mason trichrome staining for collagen was not present in the glomeruli of wild type controls, while a clear blue staining indicating the presence of collagen was present in the AS-UG kidneys. The histopathological and immunofluorescence analyses of the kidneys strongly suggests that abnormal accumulation of both Fn and collagen occurs in the renal glomeruli of AS-UG mice but not in those of the controls. Hence the AS-UG mice demonstrate a phenotype like the heterozygous UG-knockout (UG+/−) mice, which manifest abnormal deposition of Fn and collagen, although it is not as massive as found in those of the homozygous (UG−/−) animals.

AS-UG mice also develop abnormal deposition of IgA immunocomplexes in the renal glomeruli. Immunohistological analyses of the kidneys from AS-UG mice and their wild type littermates were performed using antibodies against murine-IgA, IgG and IgM. The glomeruli of wildtype mice were free of any immunofluorescence, while those of the AS-UG mice manifested readily detectable IgA-specific glomerular immunofluorescence. No IgG or IgM-specific fluorescence were detectable in the glomeruli of either wild type or AS-UG mice. These results demonstrate that suppression of UG production in the AS-UG mice results in abnormal glomerular deposition of IgA in addition to Fn and collagen, in the renal glomeruli.

In AS-UG mice, expression of UG-antisense RNA results in the suppression of UG production, and as a result these mice demonstrate renal glomerular deposition of Fn, collagen and IgA, which is virtually identical to that of the heterozygous UG-knockout (UG+/−) mice. The renal pathology in the UG-knockout mice, reported in Example 1, is due to the lack of UG expression and not due to the disruption of an unrelated gene. The use of fresh frozen sections, coupled with partial protease digestion, facilitated the detection of the IgA immunocomplexes in the glomeruli of both the AS-UG as well as UG-knockout mice.

Example 9

Sequence Variants and Fragments

The present invention is not limited to administration of native types of uteroglobin to treat IgA mediated diseases, but can also include administration of variant forms of uteroglobin (including uteroglobin fragments). Examples of uteroglobin fragments that would be expected to retain therapeutic activity are, for example, those anti-inflammatory peptides shown in U.S. Pat. No. 5,266,562: MQMNKVLDS (SEQ ID NO: 18), HDMNKVLDL (SEQ ID NO:19), MQMKKVLDS (SEQ ID NO: 20), DTMDAGMQMKKVLDS (SEQ ID NO: 21), GMASKAGAIAG (SEQ ID NO: 22), GIGKPLHSAG (SEQ ID NO: 23), GIGKPLHSAK (SEQ ID NO: 24), GWASKIGQTLG (SEQ ID NO: 25), GIGKFLHSAK (SEQ ID NO: 26), and GIGFLHSAG (SEQ ID NO: 27).

Moreover, uteroglobin and its variants can be expressed from DNA sequences that are variants of the native uteroglobin genomic or cDNA sequence. Two types of cDNA sequence variant may be produced. In the first type, the variation in the cDNA sequence is not manifested as a change in the amino acid sequence of the encoded polypeptide. These "silent" variations are simply a reflection of the degeneracy of the genetic code. In the second type, the cDNA sequence variation does result in a change in the amino acid sequence of the encoded protein. In such cases, the variant cDNA sequence produces a variant polypeptide sequence. In order to preserve the functional and immunologic identity of the encoded polypeptide, it is preferred that any such amino acid substitutions are "conservative" substitutions. Conservative substitutions replace one amino acid with another amino acid that is similar in size, hydrophobicity, etc. Examples of conservative substitutions are shown in Table 2 below.

TABLE 2

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Variations in the cDNA sequence that result in amino acid changes, whether conservative or not, are minimized in order to preserve the functional and immunologic identity of the encoded protein. The immunologic identity of the protein may be assessed by determining whether it is recognized by an anti-uteroglobin antibody; a variant that is recognized by such an antibody is immunologically conserved. Any cDNA sequence variant will preferably introduce no more than 20, for example fewer than 10 amino acid substitutions (for example, 1, 2, 3, 4 or 5 substitutions) into the encoded polypeptide.

The amino acid sequences of the human, rabbit, rat and mouse uteroglobin proteins in FIG. 1 provide examples of variants of the protein that retain therapeutic activity, and also provide guidance about positions in the sequence where substitutions can be made without affecting the biological and therapeutic activity of the protein. Portions of the sequence that are conserved across the species are less likely candidates for substitution. Resides that are not conserved across species are more likely candidates for substitutions, such as conservative amino acid substitutions. The assays in Examples 5, 6 and 7 can readily be used to screen UG variants (including fragments) and analogs for potential therapeutic activity. The UG KO mice discussed in Examples 2-4, and the anti-sense transgenic mouse of Example 8, also provide excellent in vivo systems for evaluation of potential therapeutics.

The present invention includes biologically active molecules that mimic the action of UG and its variants. The peptides of the invention include synthetic embodiments of naturally-occurring peptides described herein, as well as analogues (non-peptide organic molecules) and derivatives (chemically functionalized peptide molecules obtained starting with the disclosed peptide sequences) of these peptides that specifically inhibit the formation of IgA-Fn complexes. Each peptide ligand of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the peptide, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chain may be converted to $C_1$-$C_{16}$ alkoxy or to a $C_1$-$C_{16}$ ester using well-recognized techniques. Phenyl and phenolic rings of the peptide side chain may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide sidechains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Example 10

Recombinant Uteroglobin Production

Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to the uteroglobin protein may be used to prepare polyclonal and monoclonal antibodies against the protein. Thereafter, these antibodies may be used to purify proteins by immunoaffinity chromatography, in diagnostic assays to quantitate the levels of protein, and to localize proteins in tissues and individual cells by immunofluorescence. Sequence variants or the native protein may also be produced in *E. coli* in large amounts for functional studies.

Methods and plasmid vectors for producing recombinant proteins are described in Sambrook et al. (In *Molecular Cloning: A Laboratory Manual*, Cold Spring Harbor, N.Y., 1989, chapter 17). Such proteins may be made in large amounts, are easy to purify, and can be used to elicit an antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, Cold Spring Harbor, N.Y., 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Cold Spring Harbor, N.Y., 1989, chapter 17).

Methods of recombinant production of rabbit uteroglobin with recombinant plasmids have already been disclosed in Miele et al., *J. Biol. Chem.* 265:6427-6435, 1990, which is incorporated by reference. Plasmid pUG617 was digested with PstI to extract a 430 bp DNA fragment containing the entire coding sequence of mature uteroglobin. Since a PstI site is present in pUG617 immediately before the codon for Gly-1, PstI digestion also eliminated the sequence coding for the leader peptide present in pre-uteroglobin mRNA. The 430 bp fragment was purified by preparative agarose gel electrophoresis and subcloned into PstI-digested pKK233-3, generating pLE101. The orientation of the insert was checked by digestion with AvaI and BamHI. For the construction of pLE102, the PstI digested ends of the 430 bp DNA fragment were made blunt ended by treatment with bacteriophage T4 DNA polymerase. Plasmid pKK233-2 was digested with NcoI, and the cohesive ends were made blunt by treatment with DNA polymerase I large fragment.

Direct ligation of blunt ended uteroglobin cDNA fragment into NcoI-digested, blunt ended pKK233-2 generated pLE102. The orientation of the insert was checked by digestion with AvaI and HindIII, and the expected reconstitution of two NcoI sites at both ends of the insert was verified. For the construction of pLE103-1, plasmid pLE101 was digested with BamHI and NcoI, extracting from pLE101 a 285 bp fragment containing the lac operator, the trc promoter and the Shine-Delgardo sequence. The 4747 bp fragment was isolated by preparative agarose gel and ligated to a completely synthetic 89 bp BamHI-NcoI DNA fragment containing the 10 late promoter of bacteriophage T7, the 5'-non-translated region from bacteriophage T7 gene 10, and the Shine-Delgarno sequence from the same gene. In the synthetic DNA fragment the sequence of the "spacer" region between the Shine-Delgarno region and the ATG codon was modified with respect to the wild-type gene 10 so that the ATG initiation triplet could be included in an NcoI site.

The plasmids were expressed in *E. coli* strains JM105 (purchased from Pharmacia LKB Biotechnology Inc.) and JM109.

Recombinant production of human uteroglobin is disclosed in Mantile et al., *J. Biol. Chem.* 268:20343-20351, 1993, which is incorporated by reference. A cc10kDa (uteroglobin) expression vector system was constructed by cloning the human cc10kDa cDNA in pGEM 4Z (Promega), which was digested with PstI, and a 340 bp fragment containing the entire coding region of the mature protein plus 53 nucleotides of the pGEM 4Z polylinker was excised. This fragment was purified by preparative low melting agarose gel electrophoresis and subcloned into the PstI site of pLD101.

A monospecific polyclonal antibody against the protein was produced in the rabbit. Animals were immunized with a synthetic oligopeptide corresponding to the amino acid sequence of resides 37-55 of the protein. The antibody showed cross-reactivity to rabbit UG, but did not react with other proteins.

Recombinant proteins may be isolated from protein gels, lyophilized, ground into a powder and used as an antigen. The DNA sequence can also be transferred to other cloning vehicles, such as other plasmids, bacteriophages, cosmids, animal viruses and yeast artificial chromosomes (YACs) (Burke et al., 1987, *Science* 236:806-12). These vectors may then be introduced into a variety of hosts including somatic cells, and simple or complex organisms, such as bacteria, fungi (Timberlake and Marshall, 1989, *Science* 244:1313-7), invertebrates, plants (Gasser and Fraley, 1989, *Science* 244: 1293), and mammals (Pursel et al., 1989, *Science* 244:1281-8), which cell or organisms are rendered transgenic by the introduction of the heterologous uteroglobin cDNA.

The uteroglobin cDNA may be directly ligated to heterologous promoters, such as the simian virus SV40 promoter in the pSV2 vector (Mulligan and Berg, 1981, *Proc. Natl. Acad. Sci. USA* 78:2072-6), and introduced into cells, such as monkey COS-1 cells (Gluzman, 1981, *Cell* 23:175-82), to achieve transient or long-term expression. The stable integration of the chimeric gene construct may be maintained in mammalian cells by biochemical selection, such as neomycin (Southern and Berg, 1982, *J. Mol. Appl. Genet.* 1:327-41) and mycophoenolic acid (Mulligan and Berg, 1981, *Proc. Natl. Acad. Sci. USA* 78:2072-6). DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, 1973, *Virology* 52:466) or strontium phosphate (Brash et al., 1987, *Mol. Cell. Biol.* 7:2013), electroporation (Neumann et al., 1982, *EMBO J.* 1:841), lipofection (Felgner et al., 1987, *Proc. Natl. Acad. Sci. USA* 84:7413), DEAE dextran (McCuthan et al., 1968, *J. Natl Cancer Inst.* 41:351), microinjection (Mueller et al., 1978, *Cell* 15:579), protoplast fusion (Schafner, 1980, *Proc. Natl. Acad. Sci. USA* 77:2163-7), or pellet guns (Klein et al., 1987, *Nature* 327:70). Alternatively, the cDNA can be introduced by infection with virus vectors. Systems are developed that use, for example, retroviruses (Bernstein et al., 1985, *Gen. Engr'g* 7:235), adenoviruses (Ahmad et al., 1986, *J. Virol.* 57:267), or Herpes virus (Spaete et al., 1982, *Cell* 30:295).

These recombinant expression systems can be used for studies of uteroglobin and variant forms of this protein, for example in association with techniques such as site directed mutagenesis. Recombinant expression of uteroglobin may be used as a source of proteins to raise antibodies. The uteroglobin protein may be extracted following release of the protein into the supernatant as described above, or the cDNA sequence may be incorporated into a eukaryotic expression vector and expressed as a chimeric protein. Antibody to chimeric protein is thereafter used to purify the chimeric protein.

Example 11

Detection of Binding to Uteroglobin Receptor

Binding of uteroglobin fragments and variants to the uteroglobin receptor can be used as an assay to screen for variants that have a similar therapeutic activity to uteroglobin that interferes with IgA-Fn complex formation. Synthetic oligopeptides containing a model sequence MQMKKVLDS (SEQ ID NO: 20), or variants thereof (including M's substituted with isoleucine) can be measured for binding to the uteroglobin receptor. The Kd for each of the peptides is determined, and fragments or variants having a lower Kd than that of uteroglobin would be selected for further study (such as the in vivo studies described in the foregoing examples).

Example 12

Uteroglobin Gene Polymorphisms and Asthma

It is widely accepted that asthma is a heritable disease. See Holloway et al., Genetic Basis of Atopic Asthma, Clinical and Experimental Allergy 29: 1023-1032, 1999. Since the present disclosure has shown that uteroglobin is an endogenous anti-inflammatory protein whose expression may be down regulated in some inflammatory lung diseases, the uteroglobin gene was investigated in 22 families with asthmatic children to determine whether a genetic association existed between the uteroglobin gene and asthma.

The structure of the human uteroglobin gene is shown in FIG. 5. It exists as a single copy gene on human chromosome 11q12.3-13.1, and consists of three exons. The location of certain genetic polymorphisms is indicated by an asterisk. A single nucleotide polymorphism (SNP), designated A38G, is found at bp 38 in the non coding region of exon 1. Two short tandem repeat (STR) polymorphisms are present near the 5' end of the UG gene. Both are found about 3100 base pairs to the 5' side of the transcription start site. The ATTT repeat has been described, while the GTTT repeat was not previously known and was discovered during the genetic association studies of this example. Alleles typically contain between 2-18 copies of the ATTT repeat, and between 4-9 copies of the GTTT repeat. Other notable genetic features include 8 intronic alu repeats, and two polymorphic STRs (CTTTT, TTGC) at about +2900-+3200 base pairs relative to the transcription start site.

The techniques of polymerase chain reaction (PCR) is known to those of ordinary skill in the art. Table 3 shows PCR primers that may be used to amplify human uteroglobin gene polymorphisms.

TABLE 3

PCR primers for amplification of polymorphic sites in the human UG gene

| Primer | primer sequence | nucleotide position | PCR product (bp) |
|---|---|---|---|
| SNP | | −97 to +54 | 190 bp |
| hUG38F | 5'-GCC AAT GCC AAG TAA ATA GT-3' (SEQ ID NO: 28) | | |
| hUG38R | 5'-CAA GAG CGA AAC TCC ATC TC-3' (SEQ ID NO: 29) | | |
| STR(GTTT)m (ATTT)n | | −3217 to −2831 | 987-411 bp |
| hUG-3100TF | 5'-CAT CTT CCT TGC CCA TTT C-3' (SEQ ID NO: 30) | | |
| hUG-3100TR | 5'TGC ATC CCT CCC CTC TTA-3' (SEQ ID NO: 31) | | |

TABLE 3-continued

PCR primers for amplification of
polymorphic sites in the human UG gene

| Primer | primer sequence | nucleotide position | PCR product (bp) |
|---|---|---|---|
| STR(GTTT)m | | -3217 to -3169 | 69-89 bp |
| hUG-3100TF | 5'-CAT CTT CCT TGC CCA TTT C-3' (SEQ ID NO: 32) | | |
| hUG-3100GR | 5'-AAA TAA ATA AAC AAA CAA AC-3 (SEQ ID NO: 33) | | |
| STR(ATTT)n | | -3188 TO -2831 | 330-362 bp |
| hUG-3100AF | 5'-GTT TGT TTG TTT ATT T-3' (SEQ ID NO: 34) | | |
| hUG-3100TR | 5'-TGC ATC CCT CCC CTC TTA-3' (SEQ ID NO: 35) | | |

The A38G single nucleotide polymorphism may be amplified using hUG38F and hUG38R primers, yielding a 190 bp product. The (GTTT)m polymorphism (where m indicates number of repeats) may be amplified using hUG-3100TF and hUG3100GR, yielding a product of about 69 bp to about 89 bp. The (ATTT)n polymorphism (where n indicates number of repeats) may be amplified using hUG-3100AF and hUG3100TR, yielding a product of about 330 bp to about 362 bp. The (ATTT)n and (GTTT)m polymorphisms may be amplified together using hUG-3100TF and hUG3100TR, yielding a product of about 387 bp to about 411 bp.

The G38 Allele of the A38G SNP is Genetically Associated with Asthma

Figure 6A:
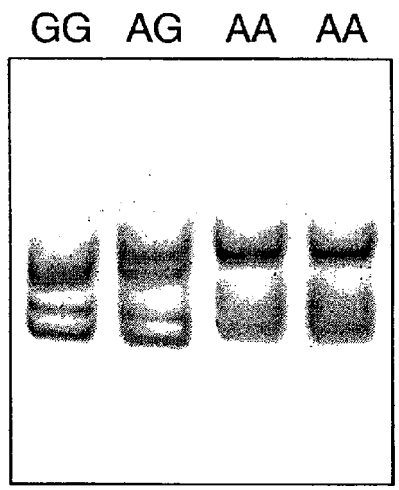
FIG. 6A shows single strand conformational polymorphism (SSCP) patterns of the noncoding region of exon 1, for AA and GG homozygotes, and AG heterozygotes.
Figure 6B:
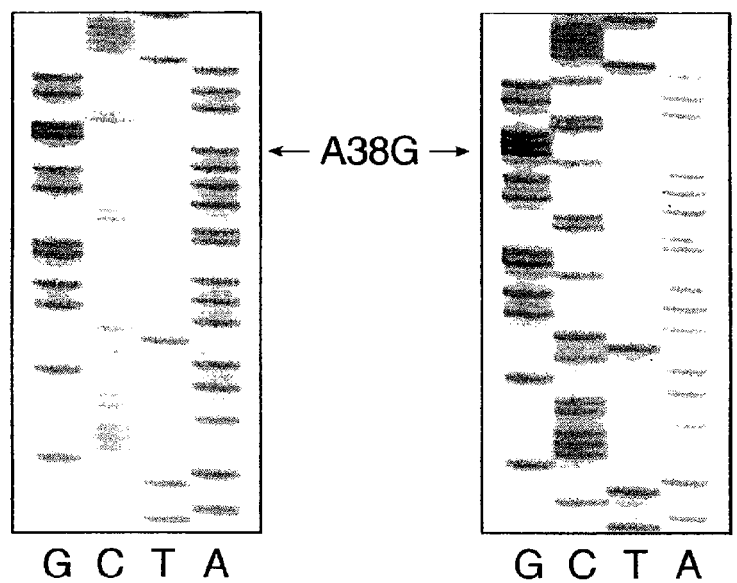
FIG. 6B shows a standard DNA sequencing autoradiogram comprising base pair 38 of the first exon of the human uteroglobin gene.
Figure 6C:
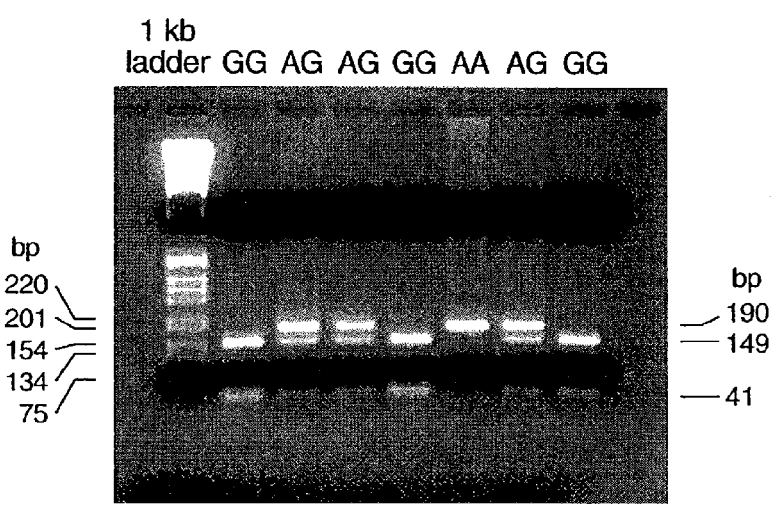
FIG. 6C shows restriction fragment length polymorphism (RFLP) patterns associated with the A38G polymorphism.

An individual's status with respect to the A38G single nucleotide polymorphism is readily determined using techniques known to those of ordinary skill in the art. FIG. 6 shows molecular analysis of alleles for the A38G SNP. FIG. 6A shows single strand conformational polymorphism (SSCP) patterns of the noncoding region of exon 1, for AA and GG homozygotes, and AG heterozygotes. FIG. 6B shows a standard DNA sequencing autoradiogram comprising base pair 38 of the first exon of the human uteroglobin gene, and compares the results obtained with the A38 allele (left) with those obtained with the G38 allele (right). FIG. 6C shows restriction fragment length polymorphism (RFLP) patterns associated with the A38G polymorphism. Fragments were generated by Sau 961 restriction digests. The A38 allele is associated with a 220 bp fragment, while the G38 allele is associated with a 149 bp fragment and a 41 bp fragment.

Using the above molecular techniques, a genetic association of the G38 allele with asthma was established. The association is presented in Table 4.

TABLE 4

Allele and genotype frequencies of A38G polymorphism

| | | Asthmatic families (N = 80) | controls (N = 42) |
|---|---|---|---|
| Genotype | GG | 0.538 | 0.381 |
| | AG | 0.463 | 0.500 |
| | AA | 0.000 | 0.119 |
| Allele | G | 0.769 | 0.631 |
| | A | 0.231 | 0.369 |
| p value | | 0.023* | |

*denote a significant difference; N, the number of individuals tested. p value was accessed by the $x^2$ test from the RxC contingency table with control group.

Asthmatic families had a 54% frequency of the GG genotype, and a 46% frequency of the AG genotype. The AA genotype was not observed. In contrast, control families had a 38% frequency of GG, 50% frequency of AG, and 12% frequency of AA. Thus, asthmatic families were significantly more likely than control families to carry the G38 allele (p=0.023, chi-square test).

A Novel Uteroglobin Short Tandem Repeat is Genetically Associated with Asthma

Table 5 presents data showing that the total number of GTTT and ATTT repeats had a significant positive correlation with the presence of asthma in kindreds (p=0.02, chi-square test).

TABLE 5

The frequencies of the total number of (GTTT)m and (ATTT)n repeats

| total number of repeats | asthmatic families (n = 160) | controls (n = 84) |
|---|---|---|
| 8 | 0.081 | 0.190 |
| 9 | 0.169 | 0.048 |
| 10 | 0.044 | 0.119 |
| 11 | 0.275 | 0.298 |
| 12 | 0.106 | 0.036 |
| 13 | 0.313 | 0.310 |
| 14 | 0.013 | 0.000 |
| p value | 0.002* | |

*denotes a significant difference; n, the number of chromosomes tested. p value was accessed by the $x^2$ test from the RxC contingency table with control group.

Tables 6 and 7 reveal that the number of GTTT repeats positively correlates with asthma presence (p=0.025, chi-square test) but the number of ATTT repeats shows no correlation (p=0.788 chi-square test). Thus, the novel GTTT polymorphism shows a genetic association with asthma. For example, when m+n is at least 8, for example 8 to 14, a statistically significant difference is noted between the asthmatic families and controls.

TABLE 6

Allele frequencies of (GTTT)m polymorphism

| Allele | asthma families (n = 160) | controls (n = 84) |
|---|---|---|
| 4 | 0.506 | 0.524 |
| 5 | 0.163 | 0.060 |
| 6 | 0.006 | 0.000 |
| 7 | 0.044 | 0.071 |

TABLE 6-continued

Allele frequencies of (GTTT)m polymorphism

| Allele | asthma families (n = 160) | controls (n = 84) |
|---|---|---|
| 8 | 0.156 | 0.286 |
| 9 | 0.125 | 0.060 |
| p value | 0.025* | |

*denotes a significant difference; n, the number of chromosomes tested. p value was accessed by the $x^2$ test from the RxC contingency table with control group. Each allele is represented by the number of repeats.

TABLE 7

Allele frequencies of (ATTT)n polymorphism

| Allele | Asthmatic families (n = 160) | controls (n = 84) |
|---|---|---|
| 2 | 0.131 | 0.143 |
| 3 | 0.175 | 0.238 |
| 4 | 0.263 | 0.262 |
| 5 | 0.019 | 0.012 |
| 8 | 0.106 | 0.071 |
| 9 | 0.294 | 0.274 |
| 10 | 0.013 | 0.000 |
| p value | 0.788 | | n, the number of chromosomes tested.
p value was accessed by the $x^2$ test from the RxC contingency table with control group. Each allele is represented by the number of repeats.

For example, when m is at least 4, for example 4 to 9, a statistically significant association was noted in asthmatic families.
Table 8 shows haplotype frequencies of (GTTT)m(ATTT)n polymorphic sites in asthmatic and control families.

TABLE 8

Haplotype frequencies of (GTTT)m(ATTT)n polymorphic sites

| Haplotype | asthmatic families (n = 160) | controls (n = 84) |
|---|---|---|
| 4-4 | 0.081 | 0.190 |
| 4-5 | 0.006 | 0.012 |
| 4-8 | 0.106 | 0.048 |
| 4-9 | 0.294 | 0.274 |
| 4-10 | 0.000 | 0.000 |
| 5-4 | 0.156 | 0.036 |
| 5-5 | 0.013 | 0.000 |
| 5-8 | 0.000 | 0.024 |
| 6-3 | 0.006 | 0.000 |
| 7-3 | 0.019 | 0.036 |
| 7-4 | 0.025 | 0.036 |
| 8-2 | 0.013 | 0.083 |
| 8-3 | 0.150 | 0.202 |
| 9-2 | 0.113 | 0.060 |
| 9-3 | 0.019 | 0.000 |
| p value | 0.002* | |

*denote a significant difference n, the number of chromosomes tested. p value was accessed by the $x^2$ test from the RxC contingency table with control group. The numbers on left and right of haplotype represent the allele of (GTTT)m and (ATTT)n sites, respectively.

For example, Haplotype 4-5 indicates 4 GTTT repeats and 5 ATTT repeats, i.e., $(GTTT)_4(ATTT)_5$. The table shows a statistically significant correlation between (GTTT)m(ATTT)n haplotype and the presence of asthma in a kindred (p=0.002, chi-square test).

Example 13

Pharmaceutical Compositions

The invention provides pharmaceutical compositions of the uteroglobin that are useful as therapeutic agents when constituted with the appropriate carriers or diluents. Hence intravenous, intramuscular or other parenteral administration are contemplated to interfere with inflammation, and in particular embodiments to interfere with IgA mediated autoimmune pathogenesis. Other available routes of administration include topical, instillation, endotracheal, pulmonary inhalation, intraperitoneal, subcutaneous, transdermal, intradermal, intracranial ventricular, intrathecal or oral administration, as are suppositories, retrograde axoplasmic transport into the brain (from the olfactory bulb) via inhalation, and ocular administration (for example in the form of eye drops).

Any of the common pharmaceutical carriers, such as sterile saline solution or sesame oil, can be used. Routes of parenteral administration include, but are not limited to, subcutaneous (sq), intracranial ventricular (icv), intrathecal (it), intravenous (iv), intramuscular (im), topical ophthalmic, subconjunctival, nasal, aural and transdermal. Peptides of the invention may be administered sq, iv or im in any conventional medium for intravenous injection, such as an aqueous saline or oil medium. The medium may also contain conventional pharmaceutical adjunct materials such as, for example, pharmaceutically acceptable salts to adjust the osmotic pressure, buffers, preservatives and the like. Among the such media are normal saline and sesame oil.

Embodiments of the invention including medicaments can be prepared with conventional pharmaceutically acceptable carriers and counterions as would be known to those of skill in the art. The medicaments are preferably in the form of a unit dose in solid, semi-solid and liquid dosage forms such as tablets, pills, powders, liquid solutions or suspensions, and injectable and infusible solutions, for example a unit dose vial. Effective dosage ranges included in the unit dose container can readily be determined from the effective concentrations shown in dose response curves, or similar curves generated for variants, analogs, mimetics, etc.

The pharmaceutical compositions may also be administered as intranasal inhalants, for example in pharmaceutical aerosols utilizing solutions, suspensions, emulsions, powders and semisolid preparations of the type more fully described in *Remington: The Science and Practice of Pharmacy* (19th Edition, 1995) in chapter 95. A particular inhalant form is a metered dose inhalant containing the active ingredient, in a suspension or a dispersing agent (such as sorbitan trioleate, oleyl alcohol, oleic acid, or lecithin, and a propellant such as 12/11 or 12/114).

Therapeutically effective doses of the compounds of the present invention can be determined by one of skill in the art, with a goal of achieving tissue concentrations that are at least as high as the $IC_{50}$ of each drug tested in the foregoing examples. The low toxicity of the compound makes it possible to administer high doses, for example 100 mg/kg, although doses of 10 mg/kg, 20 mg/kg, 30 mg/kg or more are contemplated.

The pharmaceutical compositions can be used in the treatment of a large number of IgA mediated diseases, and inflammatory conditions. Many of these conditions are associated with deposition of IgA complexes.

Another aspect of the invention is a method of treating a mammal, such as a human, having an IgA mediated condition, such as a condition in which IgA is deposited in tissue, such as glomeruli. In this aspect of the invention, the affected mammal is identified and treated with the peptide, analog or mimetic.

The above examples are provided by way of illustration only and are in no way intended to limit the scope of the invention. One of skill in the art will understand that the invention may be modified in various ways without departing from the spirit or principle of the invention. We claim all such modifications.

We claim:

1. A method of treating IgA nephropathy, comprising:
identifying a subject having an IgA nephropathy; and
administering to the subject a therapeutically effective amount of uteroglobin,
thereby treating the IgA nephropathy.

2. The method of claim 1, wherein administering uteroglobin comprises stimulating endogenous production of uteroglobin in the subject.

3. The method of claim 1, further comprising administering an additional therapeutic agent to the subject, wherein the additional therapeutic agent is effective in treating or preventing the IgA nephropathy.

4. The method of claim 3, wherein the additional therapeutic agent is a corticosteroid.

5. The method of claim 1, wherein the therapeutically effective amount of uteroglobin is administered by an endotracheal, pulmonary, inhalation, ophthalmic, intravenous, intraperitoneal, intramuscular, subcutaneous, transdermal, intradermal, intracranial, ventricular, intrathecal, or oral route.

6. The method of claim 1, wherein identifying a subject having IgA nephropathy comprises detecting deposition of IgA in glomeruli in a renal biopsy from the subject.

7. The method of claim 1, wherein the administered uteroglobin interferes with IgA-fibronectin complex formation, thereby treating the IgA nephropathy.

\* \* \* \* \*

UNITED STATES PATENT AND TRADEMARK OFFICE
CERTIFICATE OF CORRECTION

PATENT NO. : 8,084,415 B2
APPLICATION NO. : 11/934050
DATED : December 27, 2011
INVENTOR(S) : Mukherjee et al.

It is certified that error appears in the above-identified patent and that said Letters Patent is hereby corrected as shown below:

In the Specification:

At column 4, line 27, "1-Actin-mRNA," should read --β-Actin-mRNA--.

At column 17, line 7, a return carriage notation was omitted such that "Protein Deposition in Isolated Glomeruli To determine the" should read
-- Protein Deposition in Isolated Glomeruli
To determine the--.

At column 24, lines 31-32, "the 10 late" should read --the ϕ10 late--.

Signed and Sealed this
Fifth Day of June, 2012

David J. Kappos
*Director of the United States Patent and Trademark Office*

SEQUENCE LISTING

<160> NUMBER OF SEQ ID NOS: 35

<210> SEQ ID NO 1
<211> LENGTH: 70
<212> TYPE: PRT
<213> ORGANISM: Homo sapiens

<400> SEQUENCE: 1

Glu Ile Cys Pro Ser Phe Gln Arg Val Ile Glu Thr Leu Leu Met Asp
 1               5                  10                  15

Thr Pro Ser Ser Tyr Glu Ala Ala Asn Glu Leu Phe Ser Pro Asp Gln
             20                  25                  30

Asp Met Arg Glu Ala Gly Ala Gln Leu Lys Lys Leu Val Asp Thr Leu
         35                  40                  45

Pro Gln Lys Pro Arg Glu Ser Ile Ile Lys Leu Met Glu Lys Ile Ala
     50                  55                  60

Gln Ser Ser Leu Cys Asn
 65                  70

<210> SEQ ID NO 2
<211> LENGTH: 68
<212> TYPE: PRT
<213> ORGANISM: Oryctolagus cuniculus

<400> SEQUENCE: 2

Gly Ile Cys Pro Arg Phe Ala His Val Ile Glu Asn Leu Leu Leu Gly
 1               5                  10                  15

Pro Ser Ser Tyr Glu Thr Ser Leu Lys Glu Phe Glu Pro Asp Asp Thr
             20                  25                  30

Met Lys Asp Ala Gly Met Gln Met Lys Lys Tyr Leu Asp Ser Leu Pro
         35                  40                  45

Gln Thr Thr Arg Glu Asn Ile Asn Lys Leu Thr Glu Lys Ile Val Lys
     50                  55                  60

Ser Pro Leu Cys
 65

<210> SEQ ID NO 3
<211> LENGTH: 75
<212> TYPE: PRT
<213> ORGANISM: Rattus norvegicus

<400> SEQUENCE: 3

Asp Ile Cys Pro Gly Phe Leu Gln Val Leu Glu Ala Leu Leu Leu Gly
 1               5                  10                  15

Ser Glu Ser Asn Tyr Glu Ala Ala Leu Lys Pro Phe Asn Pro Ala Ser
             20                  25                  30

Asp Leu Gln Asn Ala Gly Thr Gln Leu Lys Arg Leu Val Asp Thr Leu
         35                  40                  45

Pro Gln Glu Thr Arg Ile Asn Ile Val Lys Leu Thr Glu Lys Ile Leu
     50                  55                  60

Ile Ser Pro Leu Cys Glu Gln Asp Leu Arg Val
 65                  70                  75

<210> SEQ ID NO 4
<211> LENGTH: 75
<212> TYPE: PRT
<213> ORGANISM: Mus musculus

<400> SEQUENCE: 4

-continued

```
Asp Ile Cys Pro Gly Phe Leu Gln Val Leu Glu Ala Leu Leu Met Glu
1               5                  10                  15

Ser Glu Ser Gly Tyr Val Ala Ser Leu Lys Pro Phe Asn Pro Gly Ser
            20                  25                  30

Asp Leu Gln Asn Ala Gly Leu Gln Leu Lys Arg Leu Val Asp Ile Leu
        35                  40                  45

Pro Gln Glu Thr Arg Ile Asn Ile Asn Lys Leu Leu Glu Lys Ile Leu
    50                  55                  60

Thr Ser Pro Leu Cys Lys Gln Asp Leu Arg Phe
65                  70                  75

<210> SEQ ID NO 5
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 5
ttccaaggca gaacatttga gac                                    23

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 6
tctgagccag ggttgaaagg c                                      21

<210> SEQ ID NO 7
<211> LENGTH: 23
<212> TYPE: DNA
<213> ORGANISM: Artificial sequence
<220> FEATURE:
<223> OTHER INFORMATION: Synthetic oligonucleotide primer

<400> SEQUENCE: 7
atcttgctta cacagaggac ttg                                    23

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 8
atcgccatca caatcactgt                                        20

<210> SEQ ID NO 9
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 9
atcagagtct ggttatgtgg catcc                                  25

<210> SEQ ID NO 10
<211> LENGTH: 20
<212> TYPE: DNA
```

```
<213> ORGANISM: Artificial sequence
<220> FEATURE:
<223> OTHER INFORMATION: Synthetic oligonucleotide primer

<400> SEQUENCE: 10
ggcatcgaag gtggaagagt                                          20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 11
atggccttcc gtgttcctac                                          20

<210> SEQ ID NO 12
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 12
gaaggtggtg aagcaggcat ctgagg                                   26

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 13
agaagcctgg atcccctccc                                          20

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 14
tggaacggcg tccaagagat g                                        21

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 15
ggtgtcacgg aggccaccat tactg                                    25

<210> SEQ ID NO 16
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 16
atgaaactcg ctgtcaccc                                           19
```

```
<210> SEQ ID NO 17
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 17
tacacagtga gctttgggc                                               19

<210> SEQ ID NO 18
<211> LENGTH: 9
<212> TYPE: PRT
<213> ORGANISM: Artificial sequence
<220> FEATURE:
<223> OTHER INFORMATION: Synthetic anti-inflammatory peptide

<400> SEQUENCE: 18

Met Gln Met Asn Lys Val Leu Asp Ser
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic anti-inflammatory peptide

<400> SEQUENCE: 19

His Asp Met Asn Lys Val Leu Asp Leu
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic anti-inflammatory peptide

<400> SEQUENCE: 20

Met Gln Met Lys Lys Val Leu Asp Ser
1               5

<210> SEQ ID NO 21
<211> LENGTH: 15
<212> TYPE: PRT
<213> ORGANISM: Artificial sequence
<220> FEATURE:
<223> OTHER INFORMATION: Synthetic anti-inflammatory peptide

<400> SEQUENCE: 21

Asp Thr Met Asp Ala Gly Met Gln Met Lys Lys Val Leu Asp Ser
1               5                   10                  15

<210> SEQ ID NO 22
<211> LENGTH: 11
<212> TYPE: PRT
<213> ORGANISM: Artificial sequence
<220> FEATURE:
<223> OTHER INFORMATION: Synthetic anti-inflammatory peptide

<400> SEQUENCE: 22

Gly Met Ala Ser Lys Ala Gly Ala Ile Ala Gly
1               5                   10

<210> SEQ ID NO 23
<211> LENGTH: 10
```

```
<212> TYPE: PRT
<213> ORGANISM: Artificial sequence
<220> FEATURE:
<223> OTHER INFORMATION: Synthetic anti-inflammatory peptide

<400> SEQUENCE: 23

Gly Ile Gly Lys Pro Leu His Ser Ala Gly
1               5                   10

<210> SEQ ID NO 24
<211> LENGTH: 10
<212> TYPE: PRT
<213> ORGANISM: Artificial sequence
<220> FEATURE:
<223> OTHER INFORMATION: Synthetic anti-inflammatory peptide

<400> SEQUENCE: 24

Gly Ile Gly Lys Pro Leu His Ser Ala Lys
1               5                   10

<210> SEQ ID NO 25
<211> LENGTH: 11
<212> TYPE: PRT
<213> ORGANISM: Artificial sequence
<220> FEATURE:
<223> OTHER INFORMATION: Synthetic anti-inflammatory peptide

<400> SEQUENCE: 25

Gly Trp Ala Ser Lys Ile Gly Gln Thr Leu Gly
1               5                   10

<210> SEQ ID NO 26
<211> LENGTH: 10
<212> TYPE: PRT
<213> ORGANISM: Artificial sequence
<220> FEATURE:
<223> OTHER INFORMATION: Synthetic anti-inflammatory peptide

<400> SEQUENCE: 26

Gly Ile Gly Lys Phe Leu His Ser Ala Lys
1               5                   10

<210> SEQ ID NO 27
<211> LENGTH: 9
<212> TYPE: PRT
<213> ORGANISM: Artificial sequence
<220> FEATURE:
<223> OTHER INFORMATION: Synthetic anti-inflammatory peptide

<400> SEQUENCE: 27

Gly Ile Gly Phe Leu His Ser Ala Gly
1               5

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 28
gccaatgcca agtaaatagt                                                  20

<210> SEQ ID NO 29
<211> LENGTH: 20
<212> TYPE: DNA
<213> ORGANISM: Artificial sequence
<220> FEATURE:
```

-continued

<223> OTHER INFORMATION: Synthetic oligonucleotide primer

<400> SEQUENCE: 29
caagagcgaa actccatctc                                                    20

<210> SEQ ID NO 30
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 30
catcttcctt gcccatttc                                                     19

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 31
tgcatccctc ccctctta                                                      18

<210> SEQ ID NO 32
<211> LENGTH: 19
<212> TYPE: DNA
<213> ORGANISM: Artificial sequence
<220> FEATURE:
<223> OTHER INFORMATION: Synthetic oligonucleotide primer

<400> SEQUENCE: 32
catcttcctt gcccatttc                                                     19

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 33
aaataaataa acaaacaaac                                                    20

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide primer

<400> SEQUENCE: 34
gtttgtttgt ttattt                                                        16

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide primer

<400> SEQUENCE: 35
tgcatccctc ccctctta                                                      18